US012117413B2

(12) United States Patent
Gopalakrishnan et al.

(10) Patent No.: US 12,117,413 B2
(45) Date of Patent: Oct. 15, 2024

(54) SUBSOIL MOISTURE MONITORING SYSTEM INCLUDING BATTERY-LESS WIRELESS CHIPLESS SENSORS

(71) Applicant: Purdue Research Foundation, West Lafayette, IN (US)

(72) Inventors: Sarath Gopalakrishnan, West Lafayette, IN (US); Jose Waimin, West Lafayette, IN (US); Rahim Rahimi, West Lafayette, IN (US); Nithin Raghunathan, West Lafayette, IN (US)

(73) Assignee: Purdue Research Foundation, West Lafayette, IN (US)

( * ) Notice: Subject to any disclaimer, the term of this patent is extended or adjusted under 35 U.S.C. 154(b) by 0 days.

(21) Appl. No.: 18/123,042

(22) Filed: Mar. 17, 2023

(65) Prior Publication Data

US 2023/0221274 A1 Jul. 13, 2023

Related U.S. Application Data

(63) Continuation of application No. 17/510,999, filed on Oct. 26, 2021, now Pat. No. 11,635,402.

(60) Provisional application No. 63/158,398, filed on Mar. 9, 2021, provisional application No. 63/105,456, filed on Oct. 26, 2020.

(51) Int. Cl.
*G01N 27/22* (2006.01)
*G01N 33/24* (2006.01)

(52) U.S. Cl.
CPC ......... *G01N 27/223* (2013.01); *G01N 33/246* (2013.01); *G01N 33/245* (2024.05)

(58) Field of Classification Search
CPC .............. G01N 27/223; G01N 33/246; G01N 2033/245
See application file for complete search history.

(56) References Cited

U.S. PATENT DOCUMENTS

| 8,736,452 B1 * | 5/2014 | Varahramyan | ........... H04Q 9/00 |
|---|---|---|---|
| | | | 340/539.27 |
| 2012/0161931 A1 * | 6/2012 | Karmakar | ............. G01S 13/825 |
| | | | 235/492 |
| 2017/0116444 A1 * | 4/2017 | Karmakar | .......... H01Q 15/0006 |

(Continued)

FOREIGN PATENT DOCUMENTS

| WO | WO-2020081551 A1 * | 4/2020 | ........... G01N 27/223 |
|---|---|---|---|
| WO | WO-2020121085 A1 * | 6/2020 | ......... G06K 19/0675 |

OTHER PUBLICATIONS

2015 Kim et al, "Low-Cost Inkjet-Printed Fully Passive RFID Tags for Calibration-Free Capacitive/Haptic Sensor Applications", IEEE Sensors Journal, vol. 15, No. 6, Jun. 2015 (Year: 2015).*

(Continued)

*Primary Examiner* — Eman A Alkafawi
*Assistant Examiner* — Dilara Sultana
(74) *Attorney, Agent, or Firm* — Piroozi-IP, LLC

(57) ABSTRACT

A batteryless, chipless, sensor is disclosed which includes a substrate, at least two conductive strips disposed on the substrate, a passivation layer encasing the substrate and the at least two conductive strips, wherein the conductive strips are adapted to respond to an interrogation signal from a reader having a first polarization, with a response signal at a second polarization different than the first polarization.

20 Claims, 24 Drawing Sheets

(56) References Cited

U.S. PATENT DOCUMENTS

2017/0164482 A1* 6/2017 Rogers ................. H05K 1/0286
2020/0184161 A1* 6/2020 Pettus .................. H01Q 1/2208

OTHER PUBLICATIONS

2009 Preradovic et al. "Multi-resonator-Based Chipless RFID System for Low-Cost Item Tracking", IEEE Transactions on Microwave Theory and Techniques, vol. 57, No. 5, May 2009. (Year: 2009).*

Vena et al, "A Fully Inkjet-Printed Chipless RFID Gas and Temperature Sensor on Paper", 2014 IEEE RFID Technology and Applications Conference (RFID-TA) (2014, pp. 115-120) (Year: 2014).*

A. Baumbauer CL, Anderson MG, Ting J, Sreekumar A, Rabaey JM, Arias AC, Thielens A. "Printed, flexible, compact UHF-RFID sensor tags enabled by hybrid electronics". Sci Rep. Oct. 6, 2020;10(1): 16543 (Year: 2020).*

S. K. Behera and N. C. Karmakar, "Chipless RFID Printing Technologies: A State of the Art," in IEEE Microwave Magazine, vol. 22, No. 6, pp. 64-81, Jun. 2021, (Year: 2021).*

A vena et al. "An Inkjet Printed RFID-enabled Humidity Sensor on Paper based on Biopolymer", 2nd URSI AT-RASC, Gran Canaria, May 28-Jun. 1, 2018. (Year: 2018).*

Càndid Reig, "Printed Antennas for Sensor Applications: A review", IEEE Sensors Journal, vol. 14, No. 8, Aug. 2014 (Year: 2014).*

* cited by examiner

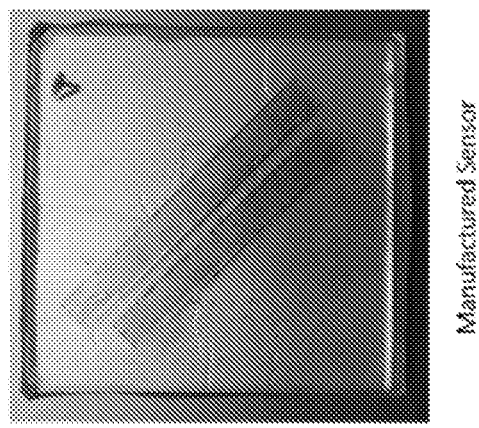
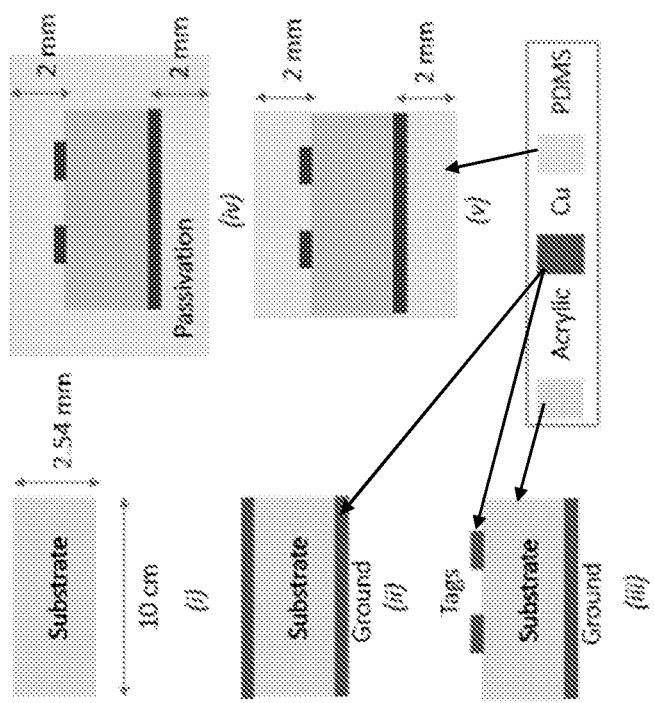
FIG. 5a
FIG. 5b (a)

(b)

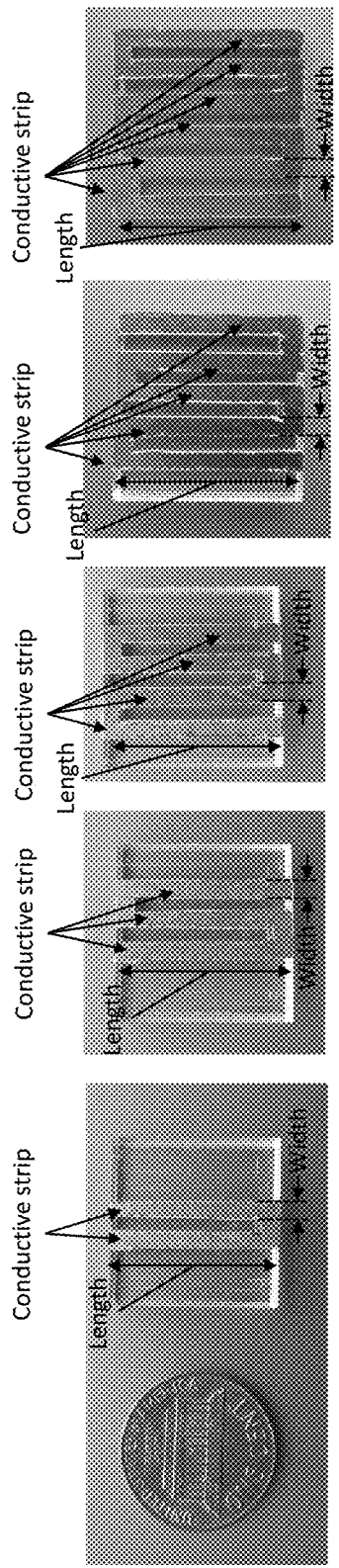

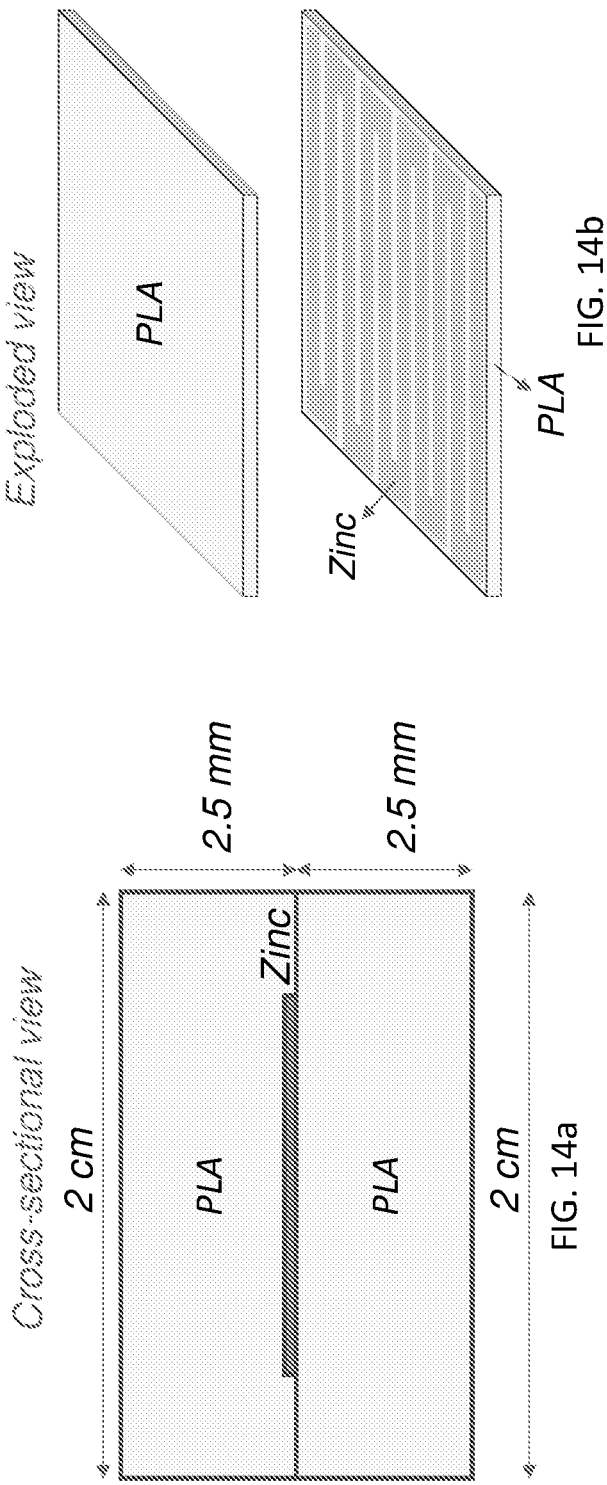
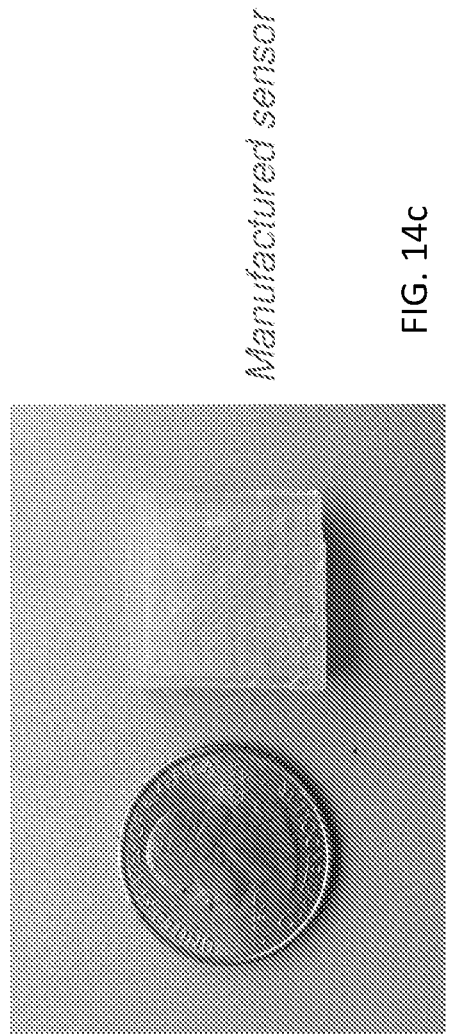
FIG. 14b
FIG. 14c
FIG. 14a

SUBSOIL MOISTURE MONITORING SYSTEM INCLUDING BATTERY-LESS WIRELESS CHIPLESS SENSORS

CROSS-REFERENCE TO RELATED APPLICATIONS

This application is a continuation application of U.S. Non-Provisional application having Ser. No. 17/510,999 titled SUBSOIL MOISTURE MONITORING SYSTEM INCLUDING BATTERY-LESS WIRELESS CHIPLESS SENSORS which was filed Oct. 26, 2021 which is related to and claims the priority benefit of U.S. Provisional Patent Application having Ser. No. 63/105,456 titled "BATTERY-LESS WIRELESS CHIPLESS SENSORS FOR SUBSOIL MOISTURE MONITORING" which was filed Oct. 26, 2020, and U.S. Provisional Patent Application having Ser. No. 63/158,398 titled "SUBSOIL MOISTURE MONITORING SYSTEM INCLUDING BATTERY-LESS WIRELESS CHIPLESS SENSORS" which was filed Mar. 9, 2021, the contents of each of which are hereby incorporated by reference in their entirety into the present disclosure.

STATEMENT REGARDING GOVERNMENT FUNDING

None.

TECHNICAL FIELD

The present disclosure generally relates to systems for monitoring subsoil conditions, and in particular, to a subsoil moisture monitoring system including battery-less wireless chipless sensors.

BACKGROUND

This section introduces aspects that may help facilitate a better understanding of the disclosure. Accordingly, these statements are to be read in this light and are not to be understood as admissions about what is or is not prior art.

The world population is predicted to reach 9.8 billion in 2050 and the food demand is estimated to increase by 59-98% between 2005 and 2050. Therefore, food productivity is an important concern in the increasing demand for sustainable agriculture. However, inattentive efforts to improve food productivity, such as unessential usage of fertilizers, have led to adverse ecological conditions including the disruption of the natural nitrogen cycle and degradation of soil quality. Precision agriculture focuses on the careful management of agricultural resources through real-time soil health monitoring at a large scale. As food demand increases, optimizing current methods of production and finding new sustainable ones becomes vitally important. Soil health monitoring for precision agriculture requires large scale deployment of sensors to monitor soil parameters such as moisture, temperature, microbial activity, nitrogen concentration etc., and to report the status of soil to farmers. Among various parameters, moisture, commonly quantified by the volumetric water content (VWC), is an important parameter in agriculture due to its influence in plant growth, nutrient transport, and soil properties. Changes in VWC have also been found to directly affect microbial biomass and enzymatic activity of microorganisms in different soil types. Microorganisms perform crucial tasks in the soil such as decomposing of recalcitrant material and are key elements in the carbon and nitrogen cycle. However, VWC measurements are limited by small-scale variations, due to geomorphological characteristics and soil properties, such as the saturated hydraulic conductivity, that occur in the spatial range of a few tens of meters and in the temporal range of a few days. To address such needs, different methods have been developed over the years.

Existing methods of VWC quantification include conventional gravimetry, wired sensing, remote sensing, and wireless techniques. The conventional gravimetric method involves collecting a sample of the soil from the field followed by weighing the sample before and after drying. The disadvantages of the gravimetric method are the laborious physical effort, the compaction of the soil during transportation and the inaccuracy caused by the water loss due to evaporation. The physical effort in moving the soil samples from the field to the laboratory can be avoided by wired sensing methods that calculate VWC by measuring the dielectric permittivity of soils.

Although a variety of sensors and probes have been developed for in situ measurement and quantification of VWC, they are limited in the fact that they need wire connection to be interfaced with external data loggers or possible wireless data transmission nodes. For example, existing technologies (imaging spectroscopy, field-deployable sensors, and passive RFIDs) used for constant monitoring of soil properties have the following drawbacks. The wired systems are slow to deploy and are at risk of being damaged by farm machinery during regular farming activity. To address this limitation, different large scale imaging systems namely, hyperspectral imagery and high-resolution satellite imagery have also been utilized in precision agriculture application. This method involves collecting images of the field and assessing the electromagnetic spectrum at fine resolution. While these image-based technologies work best for analyzing the spatial variability of crop yield, the main drawback of these methods is that they cannot be used for extracting information from beneath the ground level. Therefore, imaging spectroscopy cannot be used for extracting information from underneath the soil. Furthermore, field-deployable sensors are often wire-based, costly, and power-hungry. Passive RFID technology solves these issues through wireless communication between the reader and the sensor. While RFID based technologies are promising due to their battery-less operation, they still need electronic components for energy harvesting and sensing. Furthermore, since electronic chips are not biodegradable, burying them leads to accumulation of e-waste in the subsoil. Therefore, there is a great need for subsoil wireless sensing technologies that can be developed using fully biodegradable materials to eliminate the need for retrieval after their task has been completed in the field. In addition, to automate the process of planting sensors in the soil, the sensor needs to be small enough to fit inside a corn planter so that they can be planted during plowing without additional effort.

Therefore, there is an unmet need for a novel approach that enables convenient measurement of subsoil moisture across a large field that will not be damaged by regular farming activity.

SUMMARY

A batteryless, chipless, sensor is disclosed which includes a substrate, at least two conductive strips positioned on the substrate, and a passivation layer encasing the substrate and the at least two conductive strips. The conductive strips are adapted to respond to an interrogation signal from a reader having a first polarization, with a response signal at a second polarization different than the first polarization.

A system of determining soil conditions is also disclosed. The system includes one or more ground interrogating devices, each configured to radiate a wireless interrogation signal at a first polarization. The system also includes a plurality of ground-embedded battery-less and chipless sensors. Each such sensor includes a substrate, at least two conductive strips disposed on the substrate, and a passivation layer encasing the substrate and the at least two conductive strips. The conductive strips are adapted to receive the interrogation signal from the one or more ground interrogating devices, and in response thereto provide a response signal at a second polarization different than the first polarization. The response signal corresponds to a plurality of soil variable associated with soil conditions. The system further includes a server configured to receive signals from the one or more ground interrogating devices. Additionally the system includes at least one input/output device in communication with the server and configured to provide control signals to the one or more ground interrogating devices and to receive data associated with the soil variable associated with soil conditions.

BRIEF DESCRIPTION OF DRAWINGS

FIGS. 5a and 5b are schematics which provide manufacturing processes illustrating the fabrication steps in FIG. 5a and the final sensor form in FIG. 5b.

FIGS. 13a, 13b, 13c, 13d, and 13e are photographs of various embodiments of the sensor, according to the present disclosure in comparison to the size of a U.S. penny.

FIGS. 14a and 14b are cross sectional and perspective schematic views of the sensor of the present disclosure, respectively, chosen so that the resonant frequency is less than 1.3 GHz.

FIG. 14c is a top view of an actual reduction to practice of the sensor according to the present disclosure of the sensor shown in FIGS. 14a and 14b.

DETAILED DESCRIPTION

Figure 1A:
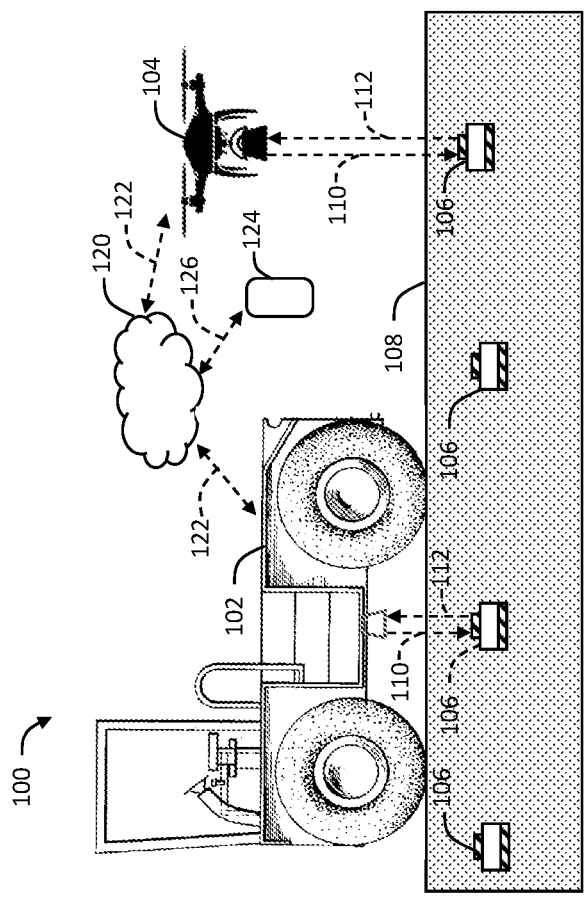
FIG. 1a is an example schematic for a system adapted to determine soil conditions utilizing one or more ground interrogating devices and a plurality of ground-embedded battery-less and chipless sensors.

For the purposes of promoting an understanding of the principles of the present disclosure, reference will now be made to the embodiments illustrated in the drawings, and specific language will be used to describe the same. It will nevertheless be understood that no limitation of the scope of this disclosure is thereby intended.

In the present disclosure, the term "about" can allow for a degree of variability in a value or range, for example, within 10%, within 5%, or within 1% of a stated value or of a stated limit of a range.

In the present disclosure, the term "substantially" can allow for a degree of variability in a value or range, for example, within 90%, within 95%, or within 99% of a stated value or of a stated limit of a range.

A novel approach that enables convenient measurement of subsoil moisture across a large field is presented that will not be damaged by regular farming activity. To address this need, here, the present disclosure presents a biodegradable battery-less chipless wireless seed sensor. This approach provides an enhanced environmental-friendly measurement technology that can be leveraged for easy deployment over a wide area. The passive chipless technology has previously been demonstrated in wireless sensing applications such as item-tracking, humidity sensing, and gas detection. Battery-less chipless sensors work based on the principle of backscattering. The interrogator-reader module includes an RF source which sends an electromagnetic signal to the sensor. This signal interacts with the sensor and reflects from its surface. The reflected signal contains the resonant frequency information of the sensor and can be detected by the reader. The resonant frequency is a function of the dimensions of the sensor and the dielectric properties of its surroundings. Using this property, non-destructive sensing of the environment is possible, by coating the sensor with a functional material sensitive to the environment, e.g., humidity, temperature, and chemical composition in the soil.

Specifically, the sensor can be coated with a biodegradable functional polymer that is sensitive to soil parameters such as moisture, temperature, nitrate concentration, and microbial activity. When the sensor is buried underneath the soil, the dielectric constants of the polymer coating and the soil change as the environmental factors change, leading to a shift in the resonant frequency of the sensor. The reader/interrogator can deduce the change in the dielectric constants of the functional polymeric coating and the soil from the interrogated resonant frequency and estimate the soil parameter under consideration.

Towards this end, a system with a plurality of passive wireless chipless sensors is presented. These sensors work based on frequency domain or time domain approaches using resonating structures that are accessed by one or more remotely positioned interrogator/reader that transmits energizing signals to the sensors. This transmitted signal interacts with the resonator and reflects from the surface of the resonator. The reflected signal contains the encoded information of the resonator/sensor and conditions of its surrounding, as discussed above. Since the passive wireless chipless sensors made of these resonators do not require onboard batteries to power them up or electronic chips to measure the parameters of interest, they are inexpensive, power efficient, integration-friendly, and printable on scalable manufacture platforms. Since subsoil telemetry requires a power-efficient, inexpensive, high-resolution measurement system to address the need for around-the-clock surveillance of spatially variable subsoil, the advantages of passive wireless chipless sensing technologies make them an ideal candidate for subsoil applications.

The interrogator/reader includes an RF source that sends the interrogation signal to the ground. The signal impinges on the sensor and backscatters from its surface. The backscattered signal is collected by the interrogator/reader. The sensors include a tag made from metallic microstrip antenna structures with a resonant frequency that is a function of the length of the tag and the effective dielectric constant of the media surrounding the tag. Due to a significant difference in dielectric properties between water (80) and dry soil (about 2), an increase in soil volumetric water content (VWC), results in a large change in the effective dielectric surrounding the sensor tag which results in a change its resonant frequency. The resonant frequency of the tags can be wirelessly measured by analyzing the spectrum of the backscattered signal received by the interrogator/reader antenna. As a result of this changes, the effective dielectric properties of the medium of interest, e.g., soil, can be extracted from the measured resonant frequency of the buried sensor tag.

The wireless reading from the sensor tags can be achieved by a single interrogator/reader module fixed onto a drone that hovers over the field, or on a field vehicle that rovers over the surface. Referring to FIG. 1a, an example of a system 100 of the present disclosure is provided. As stated above, a variety of different interrogators, e.g., a farm vehicle 102, a drone 104, etc., can be used to transmit interrogation signal to and receive response signals from one or more sensor tags 106 embedded in the soil 108. The signal paths include interrogation signals 110 emitted from the interrogators (i.e., the farm vehicle 102, the drone 104, etc.) and reflected signals 112 from the sensor tags 106. The received response signal, according to one embodiment is communicated to one or more cloud servers 120 which can be remote or local to the farming operation via a communication link 122 which can be a wired or a wireless communication link and is processed to extract the soil parameters. The one or more cloud servers 120 can then communicate soil health information to I/O devices (e.g., mobile handheld devices) 124 via a wired or wireless link 126 coupled to the one or more cloud servers 120, thereby forming a complete high spatial and temporal mapping of the VWC in the agricultural field.

A major component of the system of the present disclosure is the chipless batteryless sensor tags 106. These tags are provided and described herein in various geometries namely, hairpin resonators, slot resonators, split ring, and shorted dipoles. The choice of the tag depends on the reading method and the application. For example, according to one embodiment of the present disclosure, a wireless interrogation approach could use a linearly polarized backscattered signal. Despite the simplicity of interrogator/reader antenna in such RF based wireless integration approaches, the transmitter and the receiver are in the same polarization which results in cluttered backscatter signal readings from both the sensor tag 106 and its surroundings. In other words, when the interrogating RF signal propagates toward the sensor tag 106, it reflects not only from the surface of the tag, but also from the surrounding materials and any objects in its path. If the impeding objects do not have the ability to alter the orientation of the incident signal, they reflect the signal in the same orientation as the incident signal. Therefore, interrogator/reader receives the reflections from the clutter as well from the sensor tag in the same polarization. These undesirable RF reflections, combined with the antenna losses, increase the overall noise floor of the backscattered signal received by the interrogator/reader, thereby making it difficult to filter the desired information as shown by $S_{21(no\ tag)}$, e.g., in iteration i of FIG. 1b which provides schematics of the signal propagations according to different embodiments. Specifically, FIG. 1b (iterations i and ii) are schematics which provides a comparison between interrogator/readers of various polarizations amongst different interrogating tags. As can be seen in the panel i of FIG. 1b, the response from the tag has the same polarization as the incoming signal from the interrogator/reader (i.e., the farm vehicle 102, the drone 104, etc., shown in FIG. 1a). These undesirable reflections from the surrounding environment can be avoided by using a transmitter and a receiver that operate in cross-polarization, i.e., transmitter sends signals in the vertical polarization and the receiver receives signals in the horizontal polarization as shown in the panel ii of FIG. 1 where the noise floor, $S_{21(no\ tag)}$, is below the desired signal level, $S_{21(tag)}$, owing to the design of the tag which enables a response in a polarization that is different from the incoming interrogator/reader signal. That is in panel ii of FIG. 1b, the reflected signal from the sensor tag 106 is 90° phase-shifted with respect to the incoming (incident) signal emanating from the onboard reader/interrogator (i.e., the farm vehicle 102, the drone 104, etc., shown in FIG. 1a).

Figure 1B:
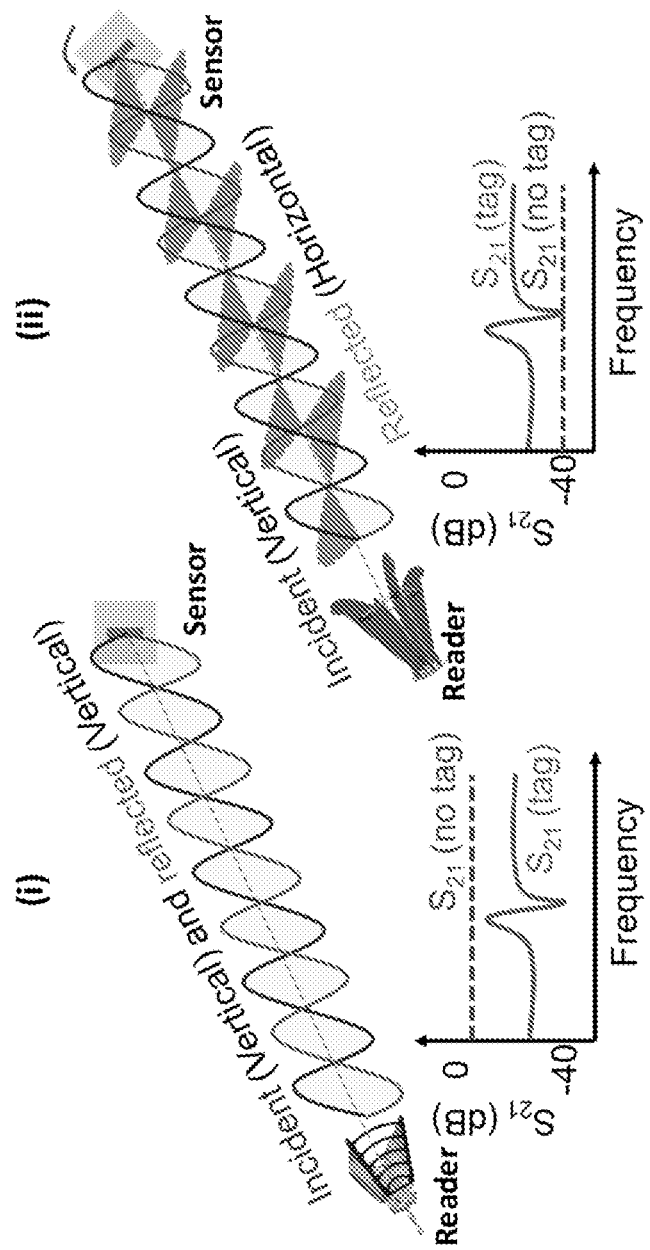
FIG. 1b represents schematics of signal propagations from the one or more ground interrogating devices and the plurality of battery-less and chipless sensors of FIG. 1a, according to different embodiments of the present disclosure.

A depolarizing sensor tag, as shown in the schematic of the panel ii of FIG. 1b, is a chipless device that can convert the vertical polarized signals received from the transmitter to both vertically and horizontally polarized signals. Depolarizing refers to the ability of a device to convert the polarization of signals that impinge on it. Here, the depolarizing sensor tag converts the polarization of the incoming signal to horizontal and vertical polarizations. The phrase $S_{21}$ in FIG. 1b and other places herein refers to the ratio of the power received at one port of a Vector Network Analyzer (VNA) coupled to the receiving section of the antenna to the power transmitted from another port of the VNA coupled to the transmitting section of the antenna. The signals from the reader antennas are vertically polarized which increases the possibility of vertically polarized reflections from the background. However, reflections from the background are less likely to be horizontally polarized. Therefore, the reflected signals from the chipless tag are less likely to be lost in the vertically polarized reflections from the background if the reflections from the chipless tag are horizontally polarized. Hence, a depolarizing tag that can receive signals in the vertical polarization but reflect them back in horizontal polarization is more likely to be noise-free. Therefore, the horizontally polarized receiver can pick up more specific horizontally polarized signals from the sensor tag with less interfering background noise.

Figure 1C:
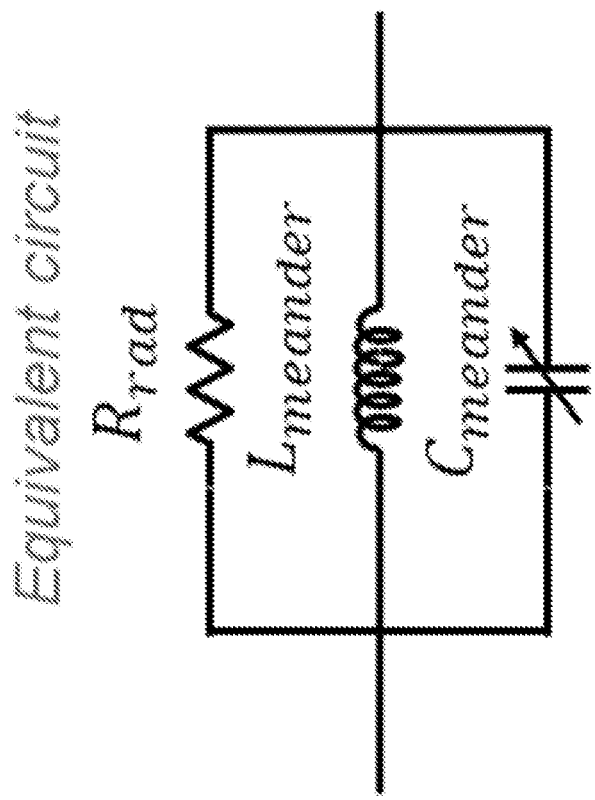
FIG. 1c is a lumped parameter schematic of the battery-less and chipless sensor of FIG. 1a, according to the present disclosure.

Referring to FIG. 1c, a lumped parameter schematic of the sensor tag according to the present disclosure is provided. The lumped parameter includes a lumped resistor ($R_{rad}$), a lumped inductor ($L_{meander}$), and a lumped capacitor ($C_{meander}$), all three provided in a parallel fashion.

One such exemplary tag includes a shorted dipole antenna when interrogated at 45° with respect to the receiver, as shown in the panel ii of FIG. 1b. In addition to the depolarizing properties, the shorted dipole structure (discussed further below), occupies less area, is centrosymmetric, and is easy to manufacture using scalable manufacturing techniques. The resonant frequency of such tags can be obtained using the following formula:

$$f_r = \frac{c}{2L_{tag}\sqrt{\varepsilon_{eff}}} \quad (1)$$

where $f_r$ is the resonant frequency;
c is the speed of light;
$L_{tag}$ is the length of the shorted dipole antenna; and $\varepsilon_{eff}$ is the effective dielectric constant surrounding the dipole antenna. By using this equation, one can roughly estimate the design parameters of the sensor tag (e.g., the sensor tags 106 shown in FIG. 1a) and its operating resonant frequency. For instance, for a shorted dipole antenna having $L_{tag}$=10 cm, and a substrate of $$\varepsilon_r = 2\left(\varepsilon_{eff} \approx \frac{\varepsilon_r + 1}{2}\right),$$

$f_r$ is approximately calculated to be 1.22 GHz.

Figure 2A:
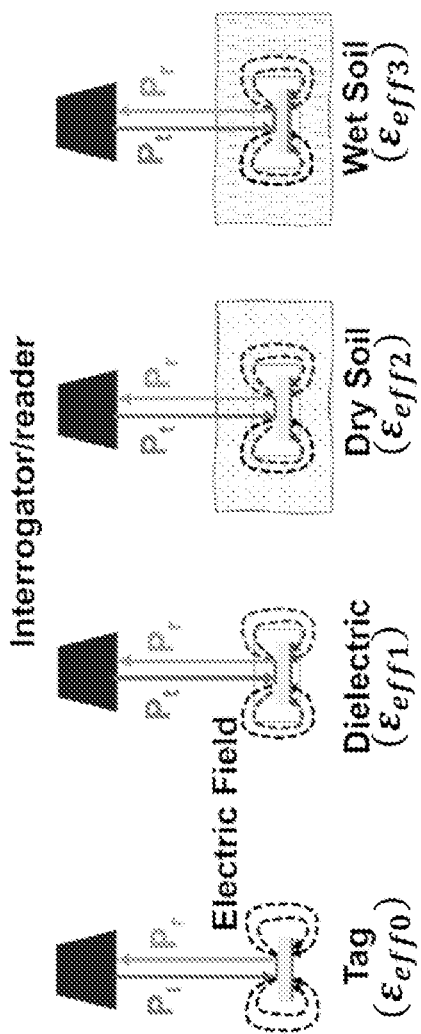
FIG. 2a provide exemplary schematics which show the working principle of the battery-less chipless sensor tag of the present disclosure.
Figure 2B:
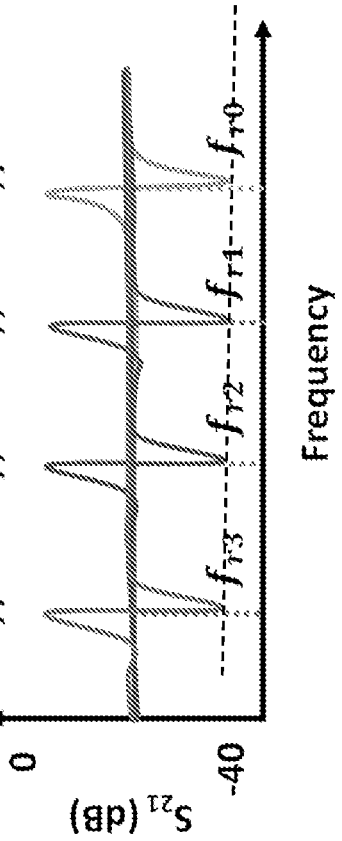
FIG. 2b is a graph of $S_{21}$ in dB vs. frequency, where $S_{21}$ represents the ratio of the power received at one port of a Vector Network Analyzer (VNA) coupled to the receiving section of an antenna receiving signal from the sensor to the power transmitted from another port of the VNA coupled to the transmitting section of the antenna.

Referring to FIG. 2a, exemplary schematics are provided which show the working principle of the battery-less chipless sensor tag of the present disclosure. FIG. 2a provides schematics illustrating the shift in the resonant frequency when the sensor is surrounded by air, a passivation layer, dry soil and wet soil. For a fixed length of the tag, the resonant frequency is a function of the effective dielectric constant ($\varepsilon_{eff}$) in the fringing electric field between the periphery of the dipole antenna and the ground plane of the tag. As illustrated in FIG. 2a, the effective dielectric constant of the as prepared tag without a passivation coating is shown as $\varepsilon_{eff0}$ which is a function of the dielectric constant of the substrate $\varepsilon_r$ and its surrounding air (about 1), resulting in an initial resonant frequency denoted as $f_{r_0}$ shown in FIG. 2b which is a graph of $S_{21}$ in dB vs. frequency. By passivating the sensor tag with a polymer coating (with dielectric constant $\varepsilon_r$ greater than air (which is about 1), the $\varepsilon_{eff}$ increases to $\varepsilon_{eff}$, which decreases the sensor's resonant frequency to $f_{r_1}$. As discussed with respect to FIG. 1a, the sensor tags are buried underneath the soil and has a resonant frequency that is dependent on the dielectric constant of the surrounding soil. As the moisture content in the soil increases, the presence of bound water (with dielectric constant of about 80) within the soil increases. This causes an increase in the $\varepsilon_{eff}$ leading to a decrease in the resonant frequency reading from the sensor. By analyzing the changes in the resonant frequency, one can wirelessly retrieve the VWC of the soil surrounding the sensor. Referring to FIG. 2b, response vs. frequency from the tags are shown for different conditions (e.g., when the sensor is surrounded by air ($f_{r0}$), passivation layer ($f_{r1}$), dry soil ($f_{r2}$) and wet soil ($f_{r3}$)). As seen in FIG. 2b, the natural frequency of the tag is lower when in contact with wet soil vs. when it is in contact with dry soil. This difference can be used advantageously to determine the wetness of the soil. The dashed line in FIG. 2a depicts the change in the natural frequency as conditions vary.

The design of the shorted dipole mainly depends on the working resonant frequencies band in which the sensor tag needs to operate. The upper limit of the band depends on the resonant frequency of the tag in air, which in turn depends on the inductance ($L_{tag}$) and the dielectric constant of the substrate ($\varepsilon_{r(sub)}$).

For effective wireless reading through soil, the working range of the sensors' resonant frequencies must support good levels of RF signal penetration into the soil while having a reasonable sensor tag size for practical field deployment. The depth of penetration of the EM signals into a soil depends on its dielectric constant and electrical conductivity. The dielectric constant of soil can range from about 5 to about 30. The range of radio waves used for ground penetration is less than about 2 GHz. According to one embodiment, frequencies between about 900 MHz and about 1 GHz are chosen for the band so that the two peaks can act as an electromagnetic identification (ID) that indicates the presence of the sensor and avoids inadvertent readings. Therefore, a two-tag configuration is used in the sensor.

Figure 3:
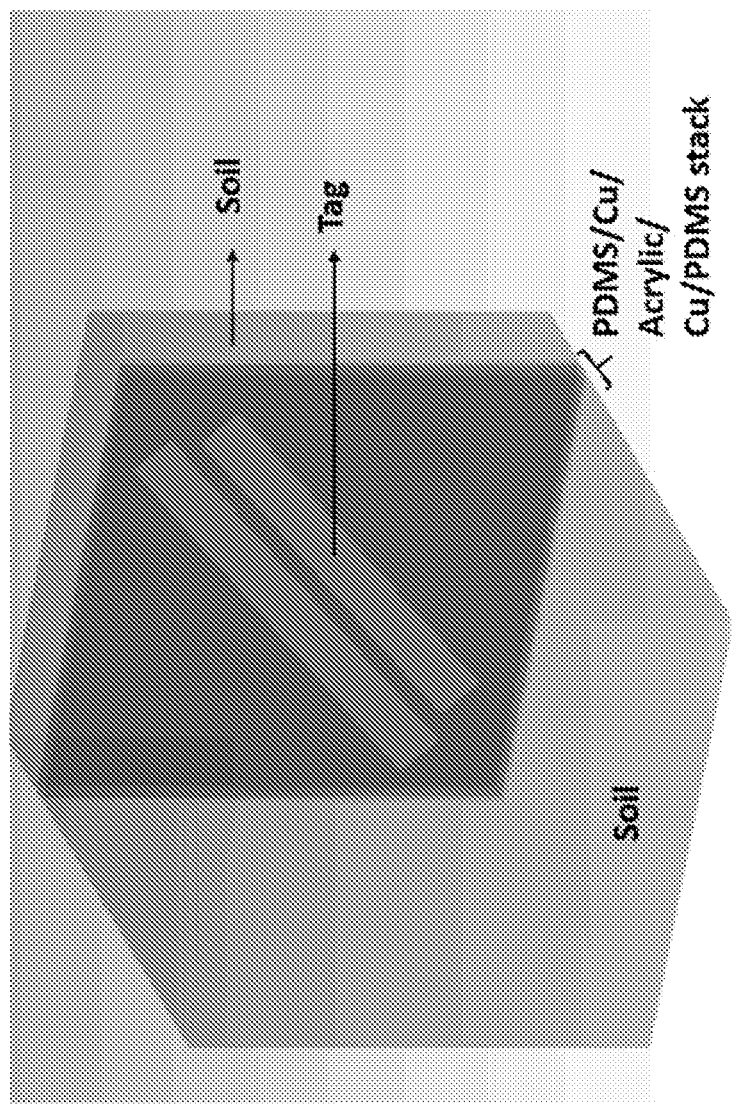
FIG. 3 is a schematic of a test setup of the sensor, according to the present disclosure.

The sensor tags of the present disclosure are simulated in CST MICROWAVE STUDIO. The simulations are performed on a sensor tag structure shown in FIG. 3, which is a schematic of the test setup. In this design, the sensor tags are assembled on to a 10 cm×10 cm×2.54 mm acrylic substrate. Tags of dimensions of 10 cm×1 cm×17.5 μm and 9 cm×1 cm×17.5 μm are placed on top of the acrylic substrate with a spacing of 4 mm. A ground plane of size 10 cm×10 cm×17.5 um is placed on the back of the acrylic substrate. A 2 mm thick layer is placed to passivate the top and bottom of the structure. A 10 cm thick layer of soil is assumed in the front and a 2 cm thick layer of soil is assumed in the back of the resulting structure. The material for the tags and ground plane are assigned to copper and that for the passivation layer to polydimethylsiloxane (PDMS). The $S_{21}$ calibrated to remove the background noise is obtained from the horizontal component of the Radar Cross Section (RCS) in CST MICROWAVE STUDIO.

Figures 4A, 4B:
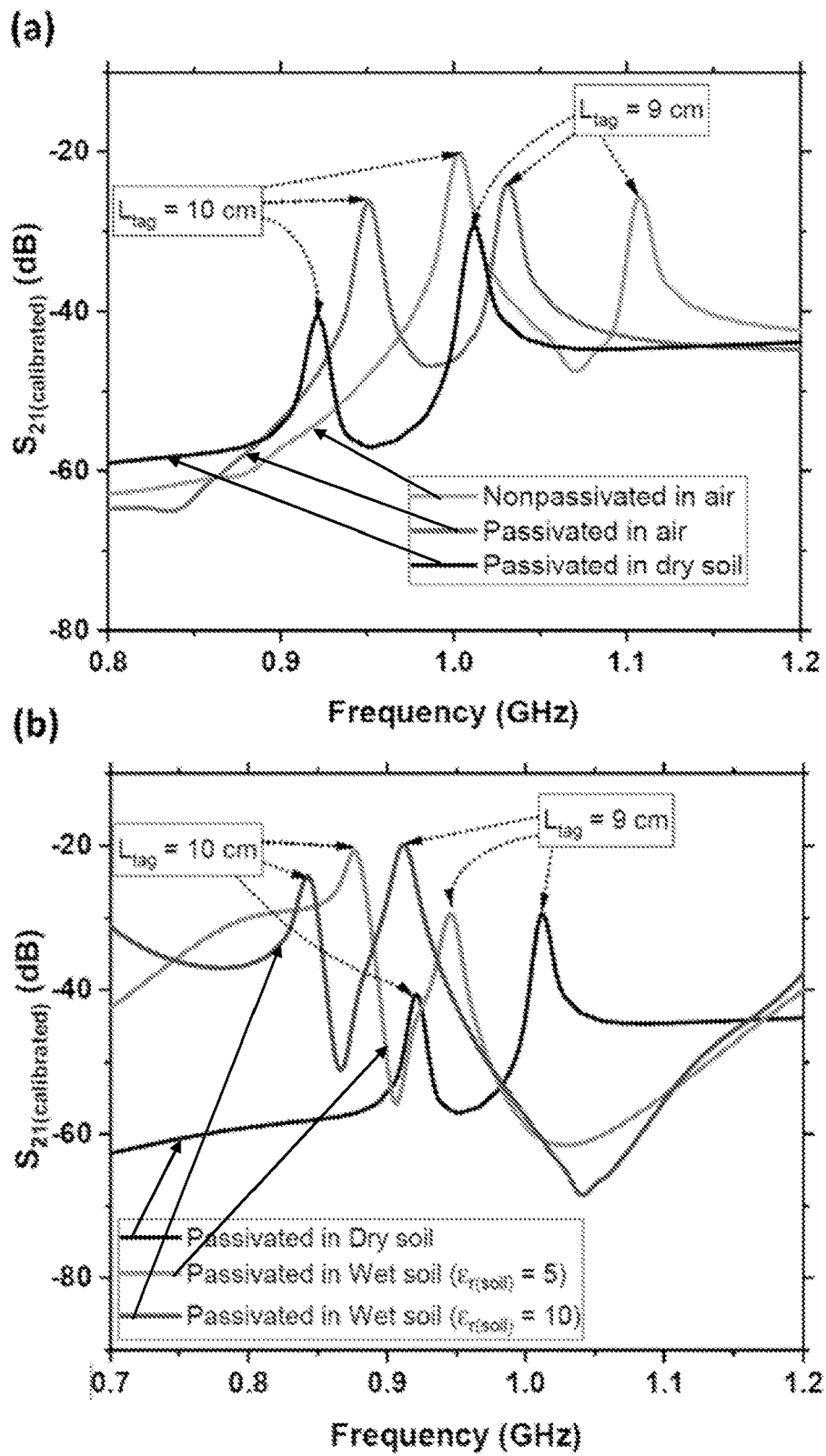
FIGS. 4a and 4b are graphs of $S_{21}$ in dB vs. frequency in Hz of results of simulations showing the working of the sensor, wherein FIG. 4a provides the results in air, in dry soil, with a passivation layer in air, and with a passivation layer in dry soil; while FIG. 4b provides the results with a passivation layer in dry soil and two different wetness levels resulting in various dielectric constants illustrated as the calibrated $S_{21}$ after passing the results through an FFT smoothing function to remove the ripples.

Referring to FIGS. 4a and 4b, results of simulations showing the working of the tags are provided: FIG. 4a provides the results in air, in dry soil, with a passivation layer in air, and with a passivation layer in dry soil; while FIG. 4b provides the results with a passivation layer in dry soil and two different wetness levels resulting in various dielectric constants illustrated as the calibrated $S_{21}$ after passing the results through an FFT smoothing function to remove the ripples. When the tag is not passivated and placed in air, $f_r$ obtained for $L_{tag}$=10 cm and $L_{tag}$=9 cm are 1.0025 GHz 1.1075 GHz, respectively. In the next simulation, the sensor is passivated with a PDMS layer of thickness 2 mm and $\varepsilon_r$ of 2.2 and is placed in air. Since the passivation layer increases the $\varepsilon_{eff}$, there is a 5.23% and 6.7% shift in the $f_r$ for $L_{tag}$=10 cm and 9 cm, respectively. This increases to 8% and 8.5% ($L_{tag}$=10 cm and 9 cm, respectively) caused by the increase in the $\varepsilon_{eff}$ when the medium is changed from air to dry soil. It should be noted that VWC of dry soil is about 2.55. However, it is lower than the frequency shift for the non-passivated sensor in dry soil because the former is contributed by materials of higher effective dielectric constant. FIG. 4b shows the shift in $f_r$ simulated with a passivated sensor in wet soil. It should be noted that VWC of the wet soil is about 18.8 when the dielectric constant is about 10. The wet soil simulations are done by increasing the $\varepsilon_{r(soil)}$. When the $\varepsilon_{r(soil)}$ is increased to 5, the shift in $f_r$ is 5% and 6.5% for $L_{tag}$=10 cm and 9 cm, respectively. The shift in $f_r$ increases to 8.45% and 10% for $L_{tag}$=10 cm and 9 cm, respectively, as the $\varepsilon_{r(soil)}$ is increased to 10 following the Eq (1).

Two types of tags are developed for the experiments. The first type of tags does not have a passivation layer. This is used in the initial experiments to demonstrate the working of the sensor in air. The second type of tag has a passivation layer. This is used in the second set of experiment used for soil measurements. The fabrication steps are shown in FIGS. 5a and 5b which provide manufacturing process illustrating the fabrication steps in FIG. 5a and the final sensor form in FIG. 5b. The process begins by providing a substrate (e.g., acrylic). Thereafter, sheets of conducting material (e.g., copper), are deposited on the substrate. Thereafter, material from the upper conducting sheet is removed leaving two strips of metal, resulting a subassembly. Thereafter, a layer of passivation (e.g., PDMS) is placed over the subassembly, and finally the passivation layer is formed to fit the size of the subassembly.

Specifically, the fabrication process shown in FIG. 5a starts with a substrate (acrylic, according to one embodiment). Based on the simulation results and the commercial availability, the thickness is chosen to be about 2.54 mm, without imposing any limitation thereon. The substrate is laser cut to form a 10 cm×10 cm layer (see FIG. 5a, panel i). Conducting material, e.g. metal, e.g., copper tapes are attached to the bottom and top as shown in FIG. 5a, panel ii.

Metal is partially removed away using a removal process (e.g., etching, laser cutting, etc.) resulting in tags on one surface, as shown in FIG. 5a panel iii. For the first set of measurements, 5 different tags are used on the same substrate. The tags are of length: 10, 9, 8, 7, and 6 cm. This sensor is used for the first set of measurements in air. For the soil measurements, the metal tapes are laser cut on the top surface to form two strips of size 10 cm×1 cm and 9 cm×1 cm (see FIG. 5b and FIG. 5a panel iii). Both strips as well as the backside of the tag are coated with a 2 mm thick passivation layer, e.g., a PDMS layer, following standard procedures (FIG. 5a panel iv). The tags are completely immersed in a solution of passivation (e.g., PDMS (1:10, cross-linker/polymer)) and degassed for 30 minutes in a vacuum chamber. The edges of the passivation layer are cured to form the final structure (as shown in FIG. 5a panel v). This forms the passivation layer that protects the tags from electrical shortage. The fabricated sensor is shown in FIG. 5b.

Two types of tags are developed for the experiments. The first type of tag does not have a passivation layer. This is used in the initial experiments to demonstrate the working of the sensor in air and dry soil. In this experiment, the ability of multiple tags to operate in conjunction with each other on the same sensor is tested and the maximum distance at which the tags can be detected in air is measured. In the dry soil measurements, the relation between the resonant frequency and the depth of the tag in the soil is studied. The second type of tag is used in soil measurements. In this experiment, water is added progressively to the sample and the percentage shift in the resonant frequency is investigated. A commercial sensor is used simultaneously to obtain ground truth values. A comparison is drawn between the frequency shift and the volumetric water content.

Figure 6B:
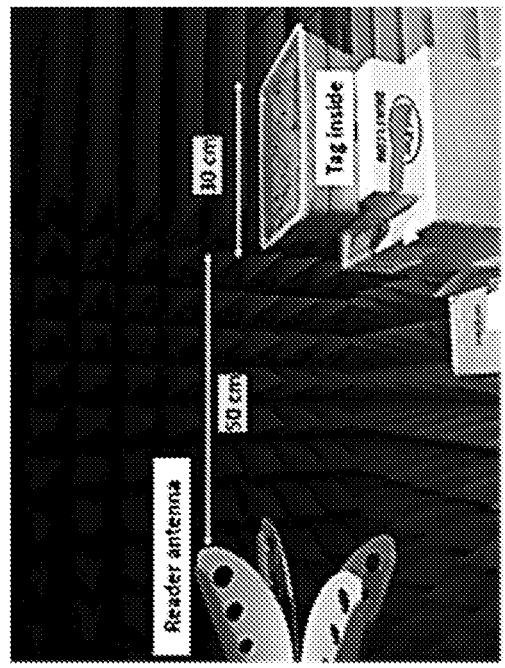
FIGS. 6a and 6b provide photographs of experimental setup with a reader antenna and the sensor in air (FIG. 6a) and in soil (FIG. 6b).
Figure 6A:
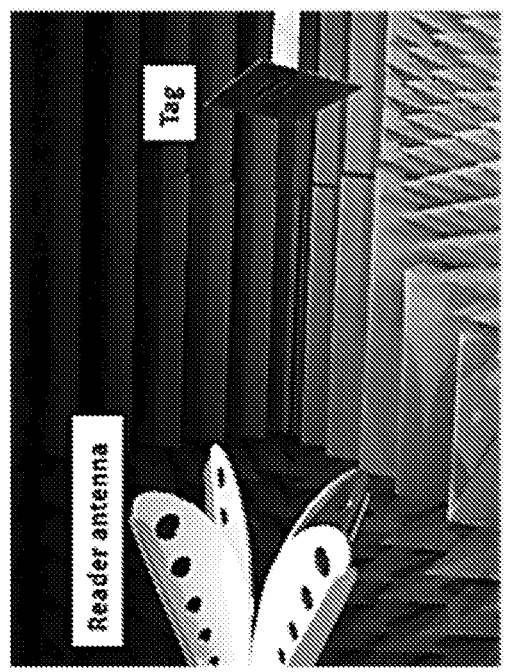

The experimental setup is shown in FIGS. 6a and 6b (photographs of experimental setup with a reader antenna and the tag in air, FIG. 6a and in soil FIG. 6b). A quad-ridge horn antenna is used as the reader. The vertical ridge is used as the transmitter (Tx) to generate a vertically polarized interrogation signal and the horizontal ridge is used as the receiver to read the horizontally polarized signal backscattered from the sensor. The vertically polarized Tx is connected to port 1 and the horizontally polarized Rx is connected to port 2 of an AGILENT NETWORK ANALYZER and the $S_{21}$ is calculated to investigate the frequency response. FIG. 6b implements the schematics in FIG. 2a. The tray is filled with soil of known volume. Water is added to the tray progressively and mixed thoroughly to make its distribution uniform throughout the tray. The experiments are performed by changing both the separation between the reader and the surface of the soil (S) and the depth of the tag under the surface of the soil (D). The effect of background is cancelled by calibrating the $S_{21}$ measurement in all the cases. This is accomplished by measuring the complex $S_{21}$ without the tag. This provides the $S_{21}$ of the background and is referred to as $S_{21(isolation)}$. The complex $S_{21}$ of the tag is also measured and is referred to as $S_{21(tag)}$. The $S_{21}$ is calibrated using the following equation:

$$S_{21}(dB)=10\log_{10}|S_{21(tag)}-S_{21(isolation)}| \quad (2)$$

Figure 7:
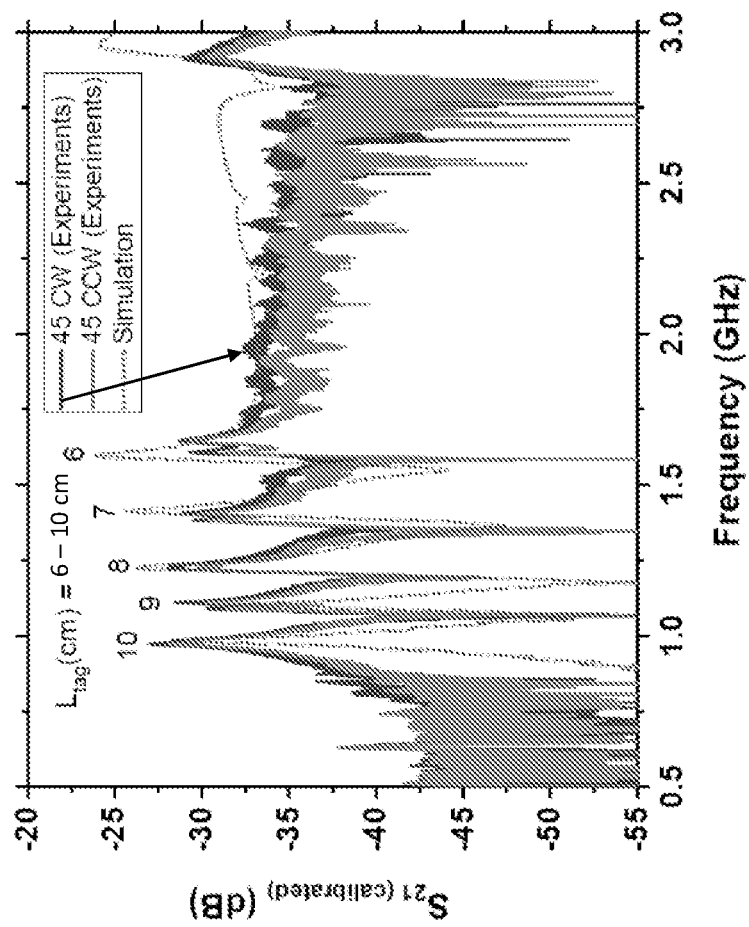
FIG. 7 provides graphs of $S_{21\ (calibrated)}$ in dB vs. frequency in GHz for multi-tag measurements with 45 degree clockwise (CW) and counterclockwise (CCW) rotations for experiments and simulations.

The calibrated $S_{21}$ measurement helps in eliminating clutter and facilitating the detection of the peak of resonance. Moreover, this measurement is simpler than RCS measurement because the latter requires an additional $S_{21}$ measurement with a structure of known RCS and the former does not. The multi-tag experiments are done in two configurations. Initially, the tag is tiled by 45° clockwise in one case and 45° counterclockwise in the other case. In both cases, the results are expected to be the same and FIG. 7, which shows graphs of $S_{21\ (calibrated)}$ in dB vs. frequency for multi-tag measurements with 45 degree clockwise (CW) and counterclockwise (CCW) for experiments and simulations, demonstrates this variation. The $f_r$ is the same for both cases at various values of $L_{tag}$. As the $L_{tag}$ increases from about 6 cm to about 10 cm with an interval of 1 cm, the $f_r$ also shifts as follows: 1.65, 1.40, 1.23, 1.1108 and 0.976 GHz. The peak of the resonance is obtained as follows as $L_{tag}$ changes from 6 cm to 10 cm: −29.09, −29.33, −28.14, −28.8, and −26.974 dB. The magnitude of the peak reduces as $L_{tag}$ changes from 10 cm to 6 cm. The $f_r$ obtained from simulation results performed on CST MICROWAVE STUDIO match exactly with the experiments. The magnitudes of the peaks show the opposite trend. However, the difference between the peaks and the notches demonstrate that the best results are obtained at the lower end of the frequencies. Furthermore, FIG. 7 illustrates a few important aspects in terms of soil applications: 1) the sensor can operate with more than one tag on the substrate without one interfering with the other. The resonant frequencies are far from each other and do not cause any interference. 2) The distance at which the tags are detectable is 2 m. Table 1 also shows that this method requires only one antenna. Bistatic measurements on the field are cumbersome because of the requirement that two interrogating device (e.g., two drones) must surveil the sensors in perfect angular alignment. Monostatic measurements are preferable, but these measurements are prone to noise when the interrogation signal and the backscattering signal are in the same polarization.

Figure 8:
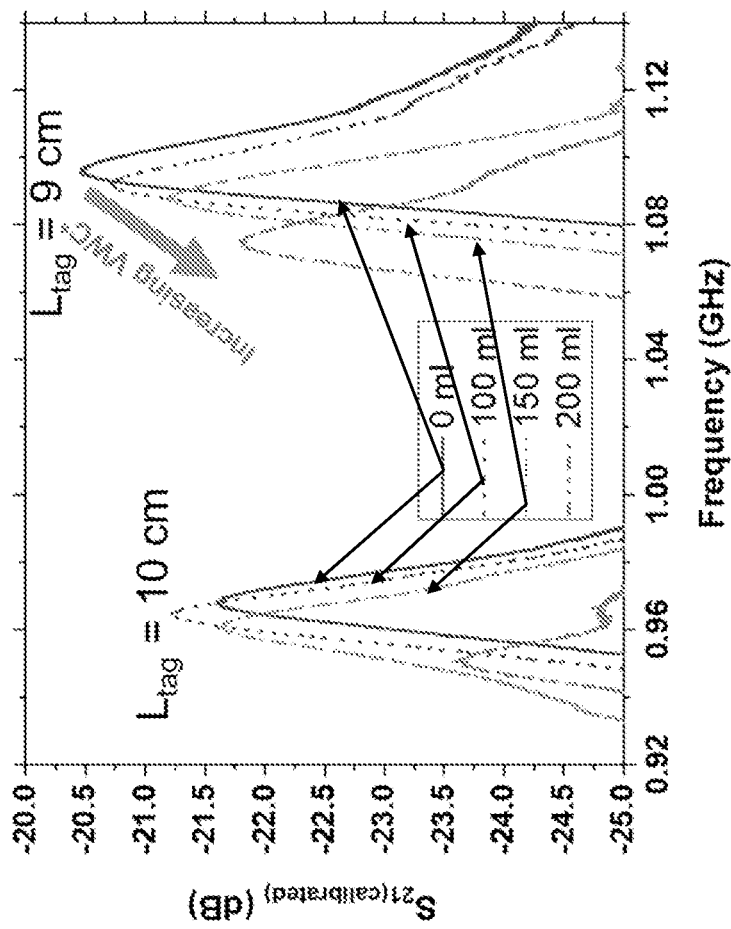
FIG. 8 provides graphs of $S_{21(calibrated)}$ in dB vs. frequency in GHz for which illustrate the response obtained when the free space distance (S) is 30 cm between the interrogator and the sensor (result are provided for wet soil experiments demonstrating shift in the resonant frequency as a function of volumetric water content (VWC) for $L_{tag}=9$ cm and 10 cm.

The soil experiments are done to study the effect of VWC on the resonant frequency ($f_r$) and the absolute frequency shift ($\Delta f_r$). The sensor is buried at a depth of 10 cm. FIG. 8 illustrates the response obtained when the free space distance (S) is 30 cm (result are provided for wet soil experiments demonstrating shift in the resonant frequency as a function of VWC for $L_{tag}$=9 cm and 10 cm). In other words, in this configuration, the tags are 9 cm and 10 cm long. The tag with $L_{tag}$=9 cm has an initial frequency of 1.096 GHz. As the water content increases in the sample, $f_r$ reduces and $\Delta f_r$ increases. At 100 ml, 150 ml, and 200 ml, $f_r$ are 1.092 GHz, 1.088 GHz, and 1.0747 GHz, respectively. This is expected because $\varepsilon_{eff}$ increases with the increase in the volume of the water added to the sample. A similar trend is observed for the $L_{tag}$=10 cm. Specifically, at 0 ml, 100 ml, 150 ml, and 200 ml, $f_r$ are 0.9678 GHz, 0.9643 GHz, 0.9607 GHz, and 0.9505 GHz, respectively, the $L_{tag}$=10 cm.

Figure 9:
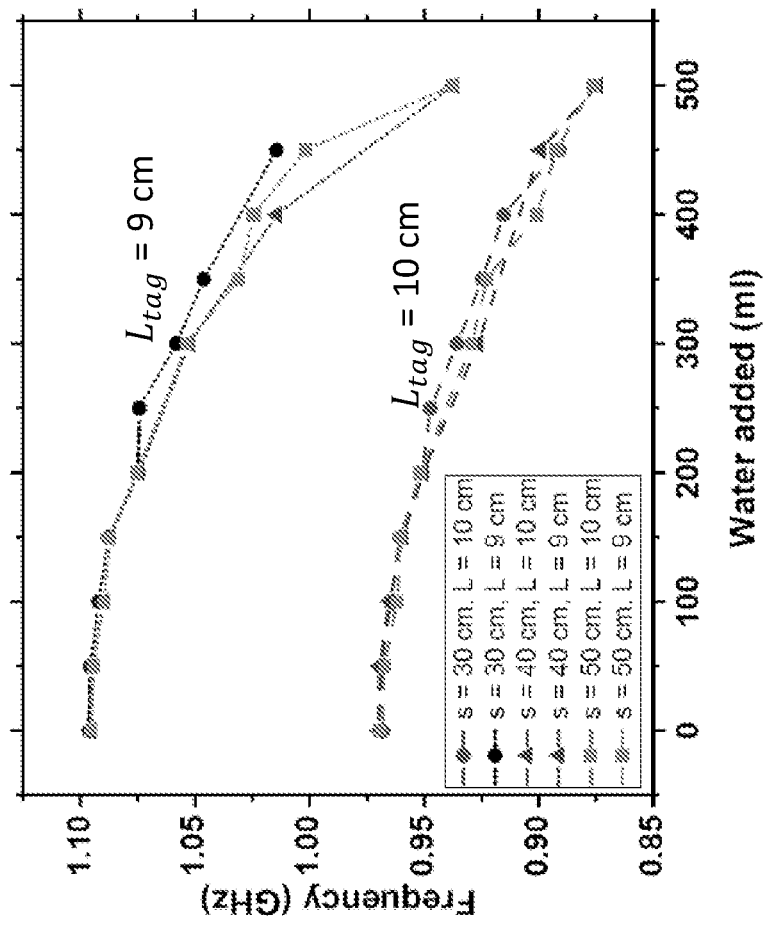
FIG. 9 provides plots of frequency vs. water added to soil sample, plotted for $L_{tag}=9$ and 10 cm when the free space distance between the interrogator and the sensor is 30, 40, and 50 cm.

The experiment is repeated for various values of free space distance such as 40 cm and 50 cm. The results are plotted in FIG. 9 (which show plots of frequency vs. water added to the sample, plotted for $L_{tag}$=9 and 10 cm when the free space distance is 30, 40, and 50 cm). From 0 ml to 200 ml, the resonant frequencies exactly follow each other. As the concentration of water increases beyond 200 ml, the error in the plots starts to increase, but is still within acceptable limits. The same trend is observed for both values of $L_{tag}$: 10 cm and 9 cm.

Figure 10A:
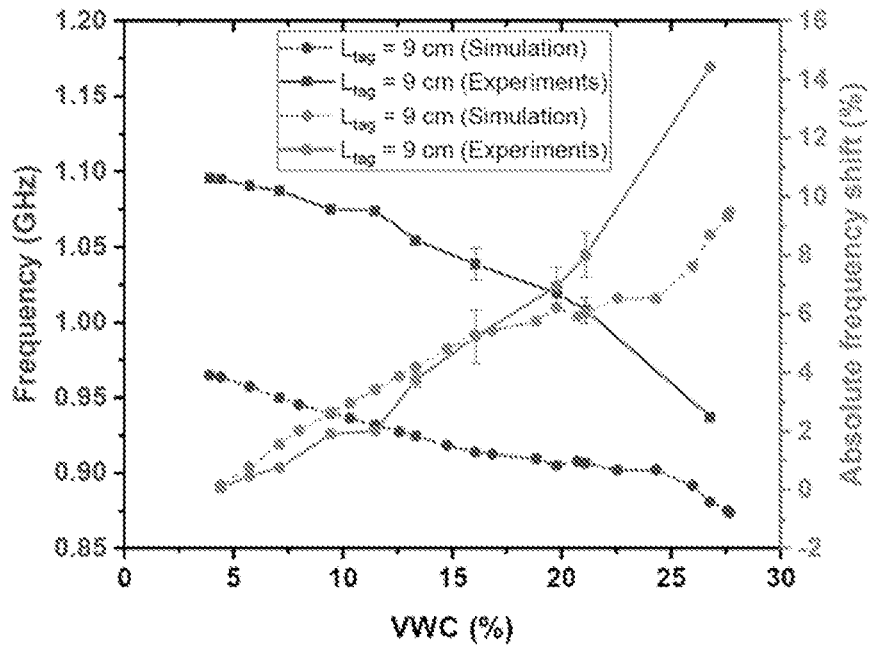
FIGS. 10a and 10b are plots which show frequency absolute frequency shift vs. VWC (%) comparing between simulation results and experimental data showing frequency and absolute frequency shift as a function of VWC for (a) $L_{tag}=10$ cm (b) $L_{tag}=9$ cm and the calculated values.
Figure 10B:
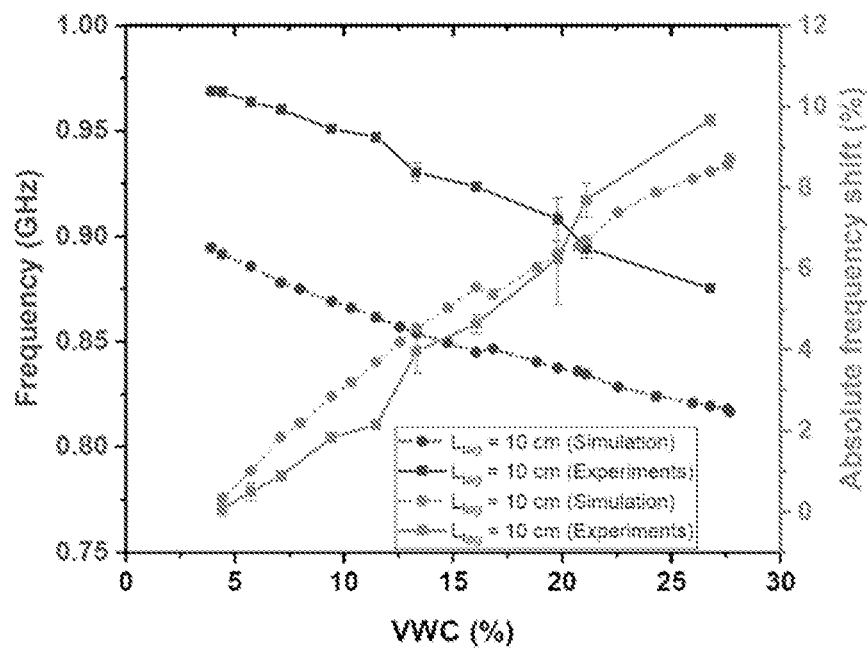

The mean value and standard deviation (SD) of the frequencies and absolute frequency shifts are depicted in FIGS. 10a and 10b (which show frequency absolute frequency shift vs. VWC (%) comparing between simulation results and experimental data showing frequency and absolute frequency shift as a function of VWC for (a) $L_{tag}$=10 cm (b) $L_{tag}$=9 cm and the calculated values). To obtain accurate measurements of the sample, a commercial sensor (DECAGON 5TE) is used for the ground truth measurement. The DECAGON sensor provides the value of the dielectric constant of its surrounding and is used for estimating the dielectric constant of the soil. The measured dielectric constant ($\varepsilon_{eff}$) is converted to VWC using the Topp equation:

$$VWC=4.3\times10^{-6}\varepsilon_{eff}^3-5.5\times10^{-4}\varepsilon_{eff}^2+2.92\times10^{-2}\varepsilon_{eff}-5.3\times10^{-2}.$$

The sensitivity of the sensor is calculated by extracting the slope of a linear fit on the plots of $f_r$ displayed in FIGS. 10a and 10b (which provide frequency vs. VWC (in %) for $f_r$ and $\Delta f_r$ for $L_{tag}$=9 cm (FIG. 10a) and $L_{tag}$=9 cm (FIG. 10b)). In the range of 4% to 22% of VWC, where the best match is obtained, the sensitivity of the sensor is calculated to be −3.92 MHz/VWC % for $L_{tag}$=10 cm and −4.85 MHz/VWC % for $L_{tag}$=9 cm in the experimental graphs. The counterparts in simulations are −3.58 MHz/VWC % for $L_{tag}$=10 cm and −3.85 MHz/VWC % for $L_{tag}$=9 cm. The sensitivity can be increased by decreasing the thickness of the passivation layer. An important advantage of this design is that the sensitivity of the sensor can be adjusted easily by changing the thickness of the passivation layer. Increasing the sensitivity also increases the bandwidth (BW) of the reader. This design provides the highest BW of 135 MHz assuming a maximum observed VWC of 27% and a sensitivity of −4.85 MHz/% VWC.

The obtained results reveal that the first order soil simulations can be used to approximate the $f_r$, $\Delta f_r$, sensitivity, and BW for a given value of VWC in any soil types by feeding the material properties of the soil into the simulator. The experiments conducted on a prototype prove the idea of this simplified simulation model has a great potential in the sensor development for agricultural applications.

Figure 11:
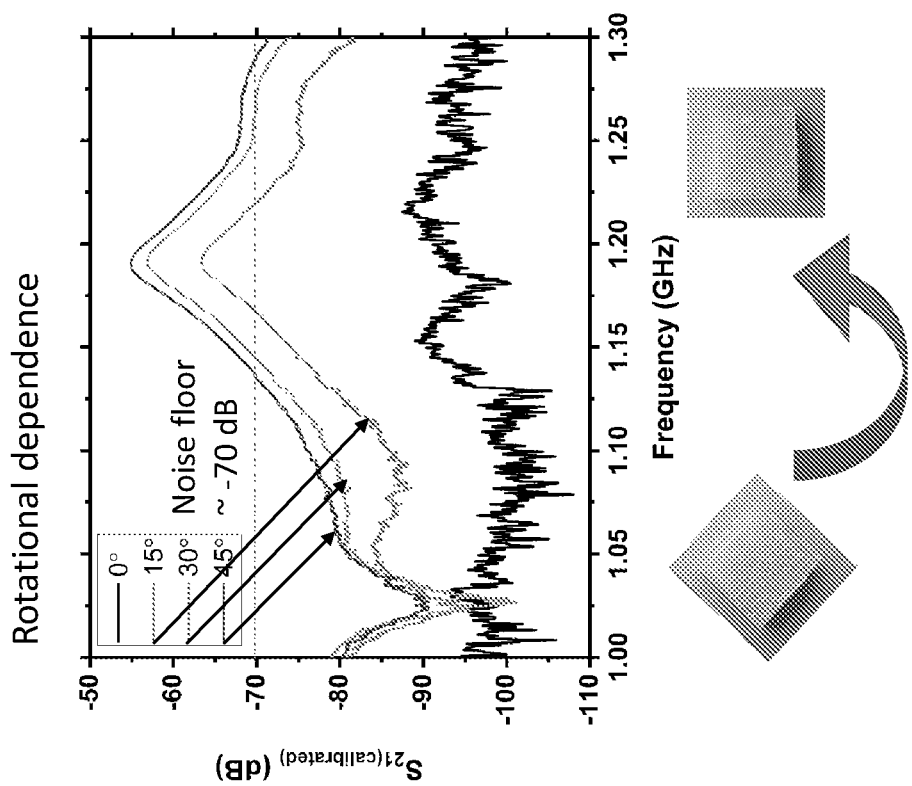
FIG. 11 a set of graphs of $S_{21(calibrated)}$ in dB vs. frequency in GHz representing angular dependence vs. frequency for different angles are provided with 45° providing the best angle.
Figure 12:
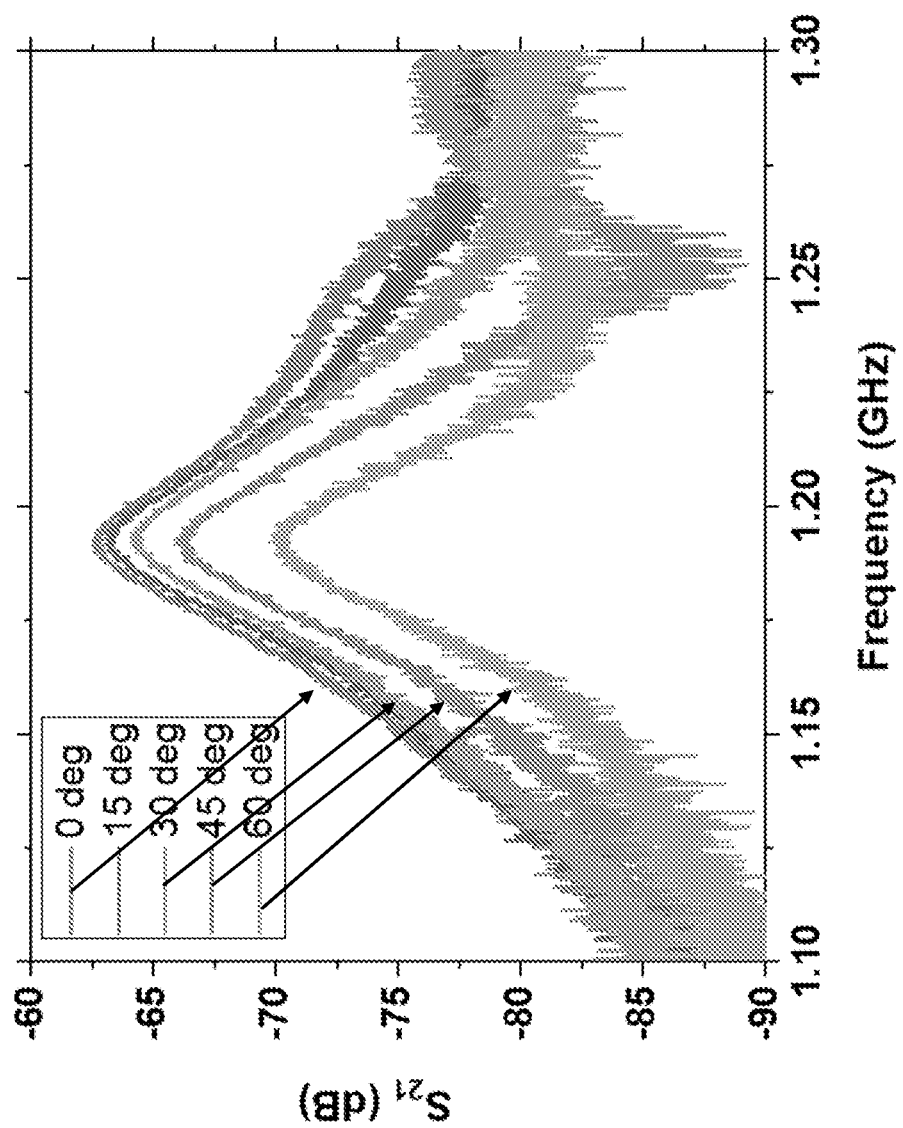
FIG. 12 is a graph of $S_{21}$ in dB vs. frequency in Hz for different rotational angles of the sensor between 0° and 60° with increments of 15°.

By defining the noise floor at −70 dB, the tag angle range for acceptable discrimination between the incident signal and the backscattered signal is identified as 15° to 75° (45° being the best case) in the first quadrant. Referring to FIG. 11, angular dependence vs. frequency is shown for different angles with 45° providing the best angle. FIG. 11 (which is a graph of $S_{21(calibrated)}$ in dB vs. frequency in HZ) shows the results for 0° to 45° rotation in 150 increments. FIG. 12 (which is a graph of $S_{21}$ in dB vs. frequency in Hz for different rotational angles of the tag between 0° and 60° with increments of 15°) shows that the sensor is centrosymmetric. Therefore, one can extrapolate the result to the entire first quadrant (0° to 90°).

If the reader is tilted, this angle can be increased to 60° relative to the horizontal plane, as shown in FIG. 12. Assuming the minimum elevation of the drone to be 1 m and the maximum line-of-sight read distance to be 2 m, the angular range, in this case, is 0° to 60° relative to the horizontal plane (i.e., ground level).

Figure 13F:
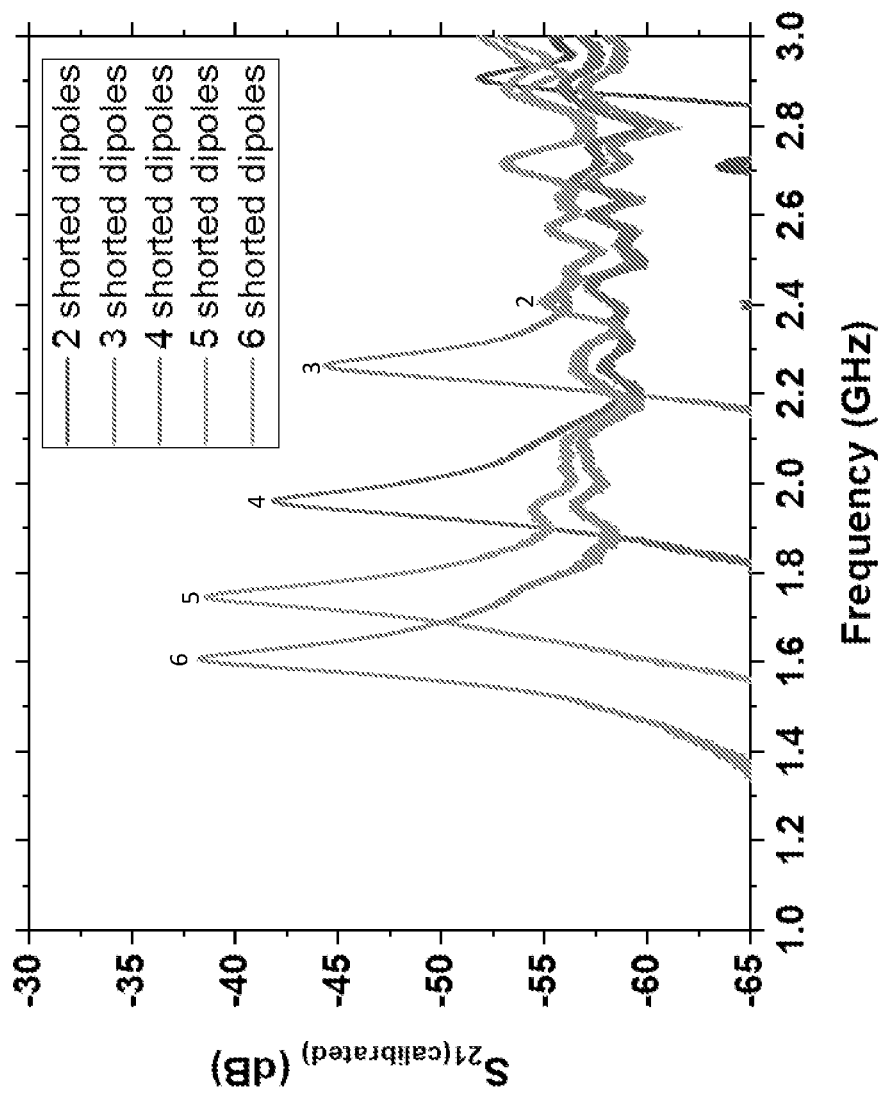
FIG. 13f is a graph of $S_{21(calibrated)}$ in dB vs. frequency in Hz for the different embodiments shown in FIGS. 13a-13e.

According to one embodiment of the present disclosure, in order to miniaturize the sensors, there are two important factors to be considered. One, the length of the sensor is inversely proportional to the resonant frequency. Two, the depth of penetration reduces with an increase in the operating frequency. For reasonable ground penetration of RF signals, the resonant frequency needs to be less than 2 GHZ, according to one embodiment. However, direct scaling of the resonator would increase the resonant frequency due to the inverse relationship between the resonant frequency and the length of the resonator. Since direct scaling cannot be used for miniaturization, a meandered line design can be implemented for redesigning the resonators, as provided in FIGS. 13a-13e (which are photographs of various embodiments of the sensor in comparison to the size of a U.S. penny). As shown in FIG. 13f, when the number of folds in the meander structure increases, the resonant frequency of the resonator reduces. For instance, when the number of shorted dipoles is increased from 2 to 6, the resonant frequency is reduced from 2.9 GHz to 1.6 GHz. Using a meandered line design, the size of the resonator is miniaturized to about 2 cm×about 2 cm thereby achieving a 25× area reduction; different embodiments are shown in FIGS. 13a, 13b, 13c, 13d, and 13e, wherein conductive strips according to different embodiments are pointed out each have substantially the same length and the same width. Results of response vs. frequency for each of these embodiments are shown in FIG. 13f (which is a graph of $S_{21(calibrated)}$ in dB vs. frequency in Hz) for the different embodiments shown in FIGS. 13a-13e. As shown in FIGS. 13a-13e and correspondingly FIG. 13f, when the number of folds in the meander structure increases, the resonant frequency of the resonator reduces (see FIG. 13f). For instance, when the number of shorted dipoles is increased from 2 to 6, the resonant frequency is reduced from 2.9 GHz to 1.6 GHz. A meandered line design that includes 10 folds, as shown in FIGS. 14a and 14b which are cross sectional and perspective schematic views of the sensor, respectively, is chosen so that the resonant frequency is less than 1.3 GHZ. A top view of an actual reduction to practice of the sensor shown in FIGS. 14a and 14b is also shown in FIG. 14c. The sensor for respective size comparison to a US coin (quarter) is shown in FIG. 14c. Using the meandered line design, the size of the resonator is miniaturized to about 2 cm×about 2 cm thereby achieving about a 25× area reduction (see FIG. 14c).

Figure 15B:
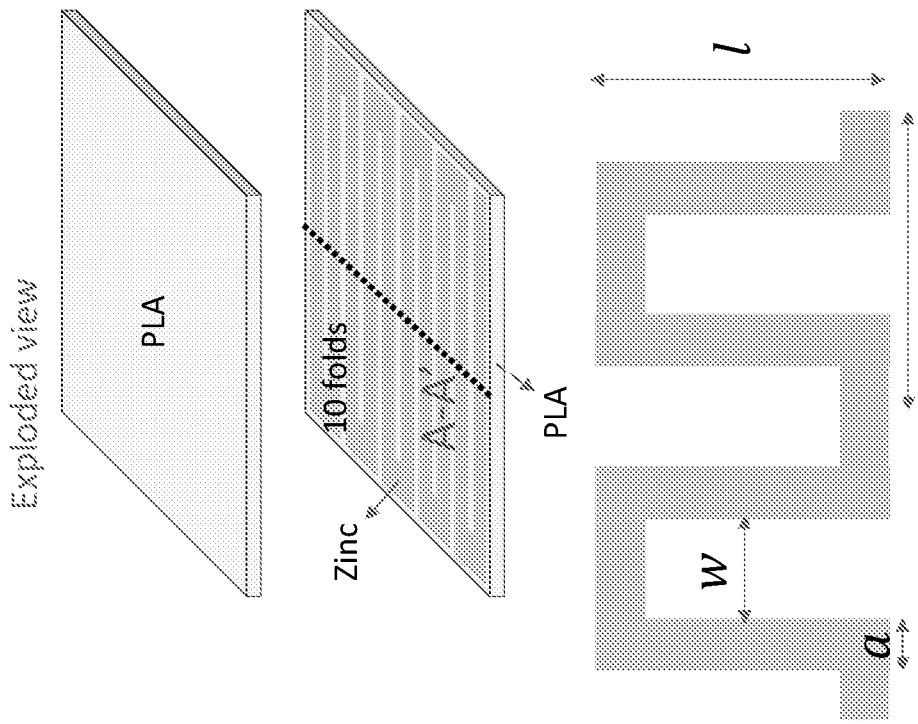
FIG. 15b provides cross-sectional parametric view of the sensor shown in FIG. 15a of a cross-section 'A-A' shown in FIG. 15b depicting an exploded and schematic view of the sensor with 10 folds.
Figure 15A:
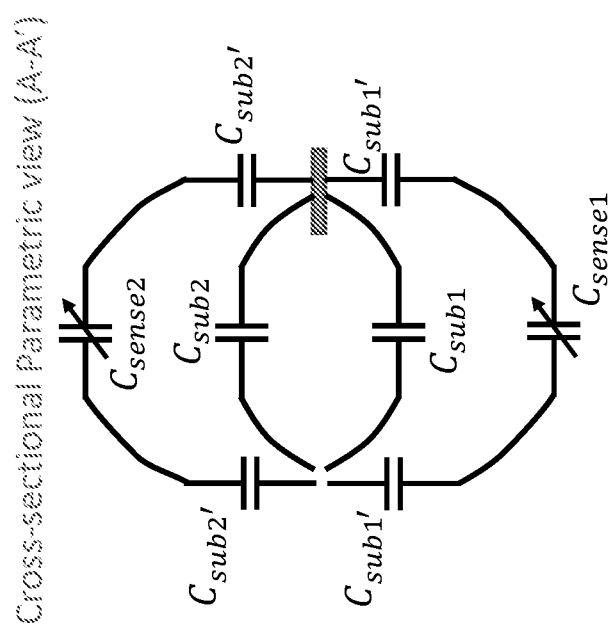
FIG. 15a is a schematic of the electrical equivalence of the sensor in an RLC parallel circuit.

The electrical equivalence of the device is an RLC parallel circuit, as shown in FIGS. 15a and 15b which are cross-sectional parametric view (FIG. 15a) of a cross-section 'A-A' shown in FIG. 15b depicting an exploded and schematic view of the sensor with 10 folds. The equations governing the values of inductance, capacitance, and resistance is provided in (3-5) below:

$$L_{meander} = 0.2L\left\{\left[1.4813\ \log\left(\frac{2L}{a}\right)\right]^{1.012} - 0.6188\right\}\mu H, \quad (3)$$

$$C_{meander} = \frac{C_{bend}}{N}, \quad (4)$$

$$R_{rad} = 34.15\left(2\pi\frac{(L-2wN)}{\lambda}\right)^{1.8}, \quad (5)$$

where N is the number of bends,
L is the total length of the meander structure,
w is the gap between the bends,
a is the radius of the trace,
$C_{bend}$ is the capacitance between adjacent bends, and
$\lambda$ is the wavelength. Accordingly, the resonant frequency is approximately proportional to the inverse square root of $L_{meander}$ and $C_{meander}$. Therefore, the resonant frequency can be reduced by increasing $L_{meander}$. Since $L_{meander}$ increases as a function of the number of bends in the structure, the resonant frequency can be reduced by increasing the number of meanders. It is to be noted that the increase in $L_{meander}$ is more dominant than the decrease in $C_{meander}$ leading to reduction in the resonant frequency as the net result. This approach helps in obtaining a 25× area reduction while retaining the resonant frequency within the range that supports good ground penetration. Sensors of this dimension can be easily distributed in the soil up to a depth of 10 cm with the help of a standard agricultural planter. Since corn seeds are typically planted at a depth of 5 cm, the sensor can be safely read.

Figure 16:
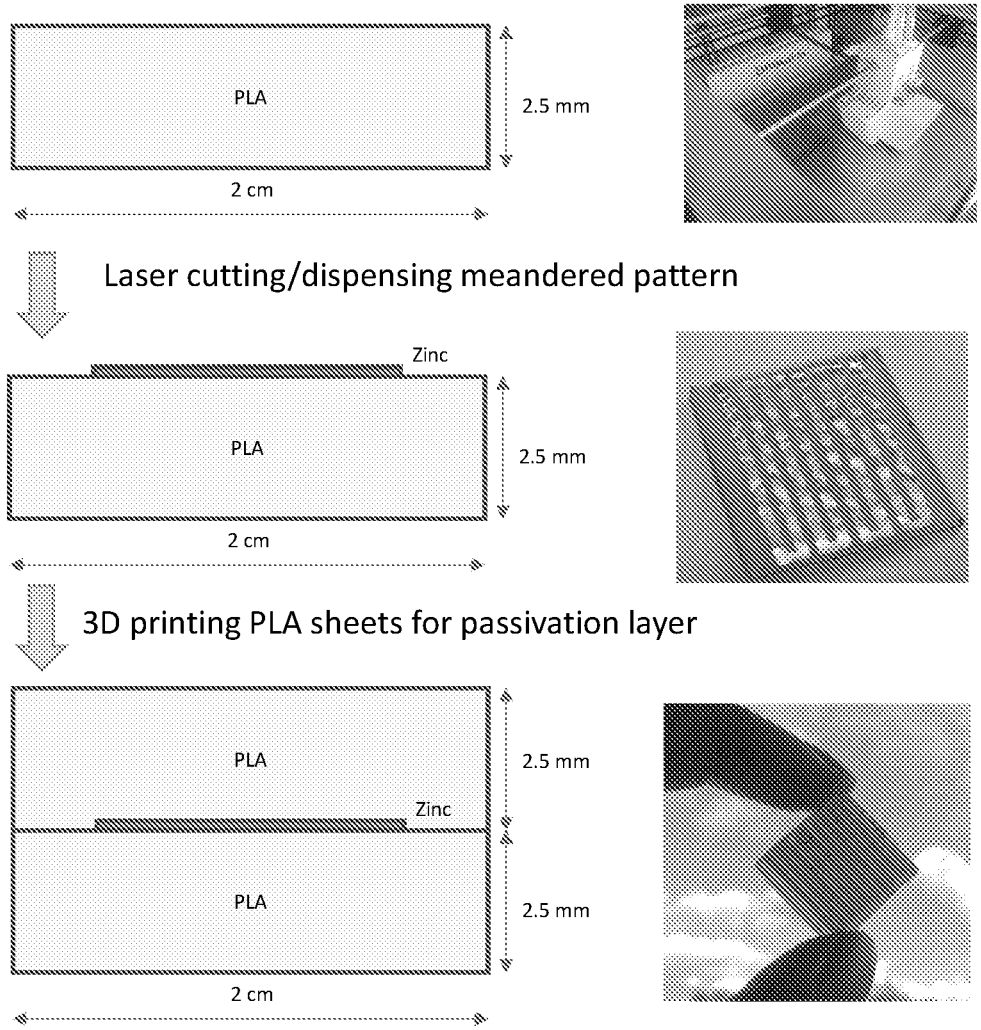
FIG. 16 provides a flow of the manufacturing process for manufacturing the sensor tag, according to the present disclosure.

A manufacturing process according to one embodiment is now provided with reference to FIG. 16 (which provides a flow of the manufacturing process of the sensor tag, according to the present disclosure). Wireless passive sensing tags are manufactured through standard scalable manufacturing techniques as shown in FIG. 16 which allow for a sustainable production of biodegradable devices. Clear solid substrates are manufactured using an ULTIMAKER 3D printer with polylactic acid (PLA). PLA is a commercially available thermoplastic which is a well-known biodegradable material, widely used in additive manufacturing applications due to its low melting temperature, low cost, and biodegradability. Despite being a biodegradable polymer, PLA is a robust material, which is insoluble in water, capable of performing while buried in the soil for months. The passivating layer covering the meandered structure can be similarly printed on top of the original PLA substrate by taking advantage of the fact that PLA does not need a hot printing platform in order to yield proper structures.

The conductive meandered structures that make up the resonator on the sensor of the present disclosure, in particular as discussed herein with respect to FIGS. 14a, 14b, 14c, 15a, and 15b, are made using biodegradable conductive zinc tape and a high-power laser source. Interest in the use of zinc as an alternative to traditional conductive materials has increased in recent years due to zinc's properties as a highly conductive, biodegradable, and biocompatible material. The meandered structure was cut using a UNIVERSAL LASER SYSTEM PLS6MW by engaging the material with a fiber laser. Through this method, conductive traces can be created at high resolution without the need of hazardous chemicals and expensive, labor-intensive techniques. Due to the efficiency of laser cutting, thousands of structures can be prepared in a matter of hours.

Figure 17:
FIG. 17 is a photograph of placement of the sensor of the present disclosure into a volume of soil.
Figure 18:
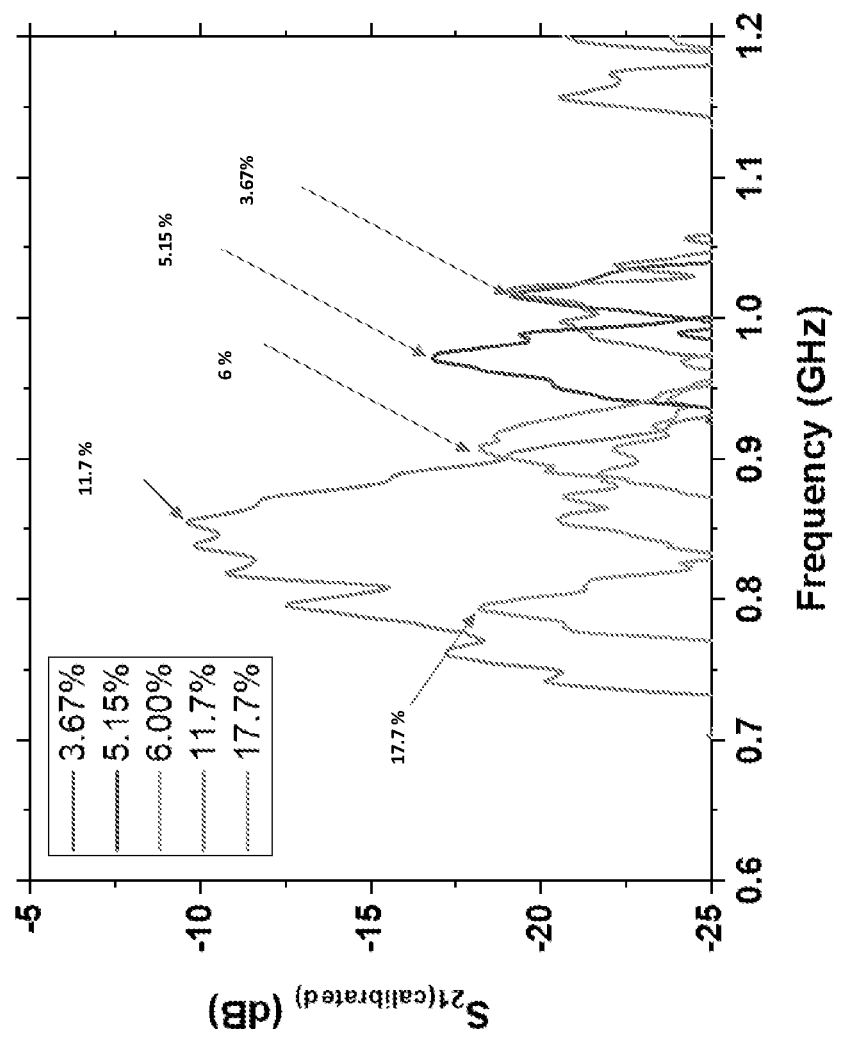
FIG. 18 is a complex set of graphs of several frequency responses vs. frequency for different values of VWC.

The sensors of the present disclosure, in particular as discussed herein with respect to FIGS. 14a, 14b, 14c, 15a, and 15b, are tested using a portable reader setup. The reader comprises of a portable VNA connected to a portable dual-polarized log periodic antenna. The sensors are placed at a depth of 5 cm in a soil sample, as shown in FIG. 17 which is a photograph of placement of the sensor of the present disclosure into a volume of soil. The VWC is changed by adding water to the soil sample and manually mixing the sample until the commercial VWC sensor shows a uniform distribution of water in the sample. The vertically polarized ridge of antenna transmits the signals to the sensor buried in the soil. The backscattered signals are collected by the horizontally polarized ridge of the antenna. The results are shown in FIG. 18 which is a complex graph of several frequency responses vs. frequency for different values of VWC. When the soil is dry (VWC=3.67%) the resonant frequency is 1.02 GHz. As the soil VWC is increased to 5.15%, 6%, 11.7% and 17.7%, the resonant frequency shifts to 0.97 GHz, 0.91 GHz, 0.85 GHz, and 0.79 GHz respectively.

Figure 19A:
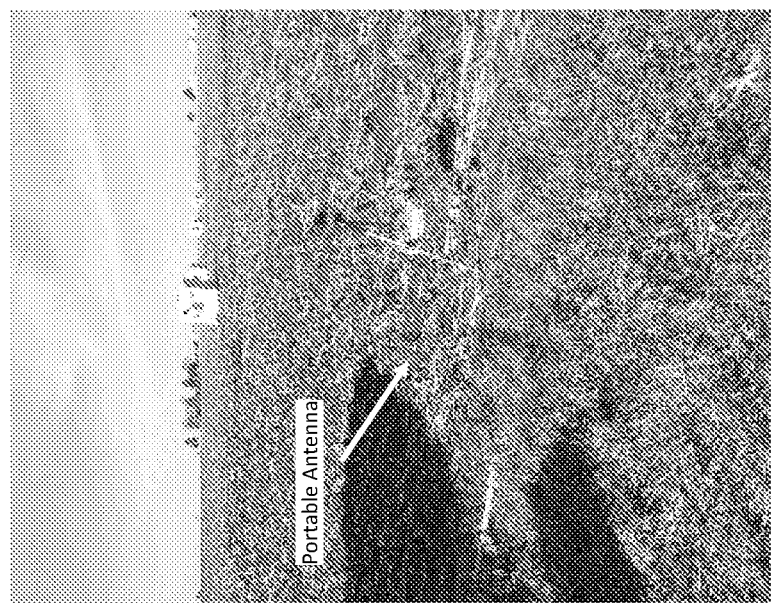
FIGS. 19a and 19b are photographs of deployment of the sensor of the present disclosure into ground and placing the interrogator at different heights.
Figure 19B:
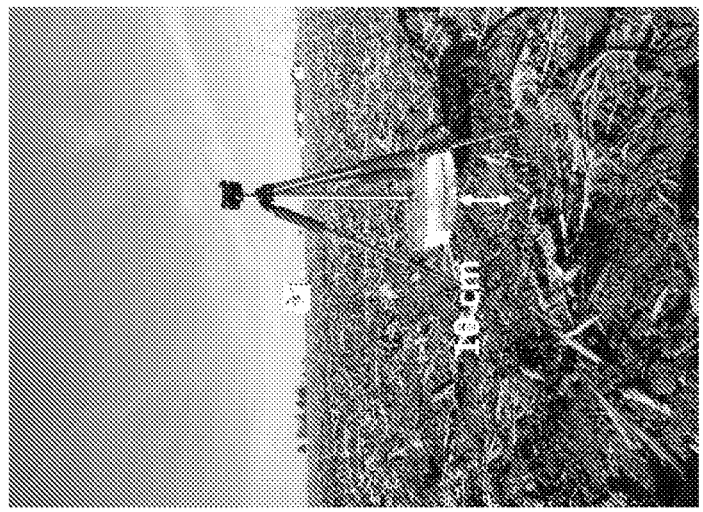
Figure 19B:
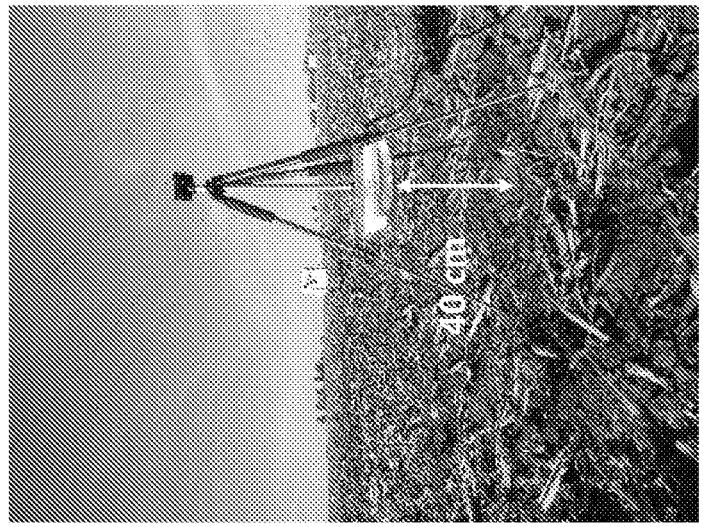
Figure 19C:
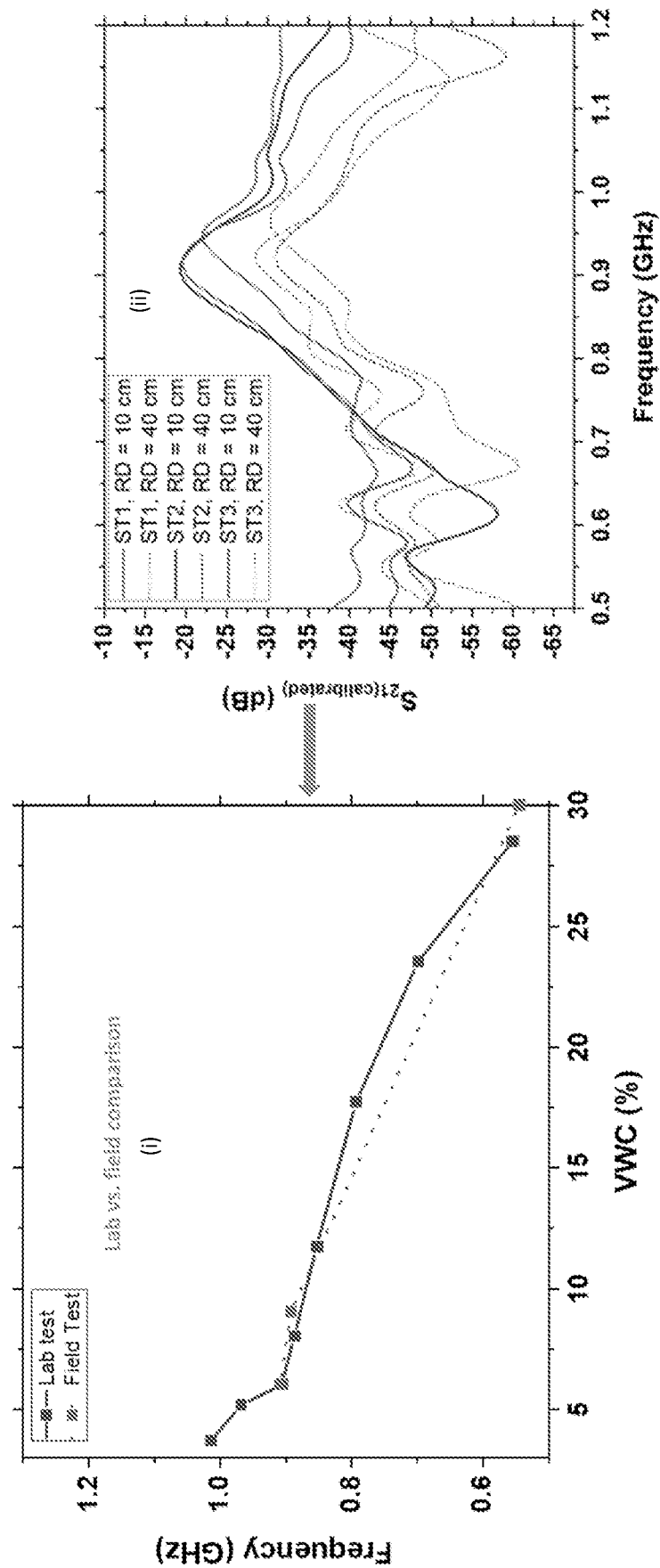
FIG. 19c provide graphs in two panels (i and ii) comparing laboratory results vs. field results which in one panel (ii) provides response vs. frequency for different measurement heights for each of the three identical sensors as shown in FIGS. 14b and 15b and in the other panel (i) compares these measurements to the laboratory measurements.

In order to test the working of the sensor in a practical scenario, several experiments were performed in an agricultural field, as shown in FIGS. 19a and 19b which are photographs of deployment of the sensor of the present disclosure (e.g., see FIG. 15b) with sensing/interrogation units disposed at different heights from the sensor. The antenna is mounted onto a height-adjustable holder and placed in the field. Three identical sensors as shown in FIGS. 14b and 15b are deployed in the field to confirm the repeatability of the measurements. The sensors are tested at heights 10 cm and 40 cm, as shown in FIG. 19b. The tests performed on different days demonstrate variation in the field conditions leading to different values of VWC. A commercial sensor is used to obtain VWC values for comparison. The measurements recorded by the portable reader matches with the values obtained under laboratory conditions, as shown in FIG. 19c which are graphs provided in two panels (i and ii) comparing laboratory results vs. field results which in one panel (ii) provides response vs. frequency for different measurement heights for each of the three sensors and in another panel (i) compares these measurements to the laboratory measurements. Moreover, the readings obtained from all the three sensors show minimal variation, hence validate the repeatability of the sensor manufacturing process.

This technique can be adapted for accurately measuring other types of soil parameters by simply changing the functional polymer films on the sensor that are sensitive to the measured parameters such as temperature, nitrate concentration, and microbial activity detection.

Those having ordinary skill in the art will recognize that numerous modifications can be made to the specific implementations described above. The implementations should not be limited to the particular limitations described. Other implementations may be possible.

The invention claimed is:

1. A batteryless, chipless, sensor, comprising:
a sensor suitable for subterranean application having a sensor body consisting of:
   a substrate;
   at least two conductive strips connected to each other and disposed in a meandered profile on the substrate, wherein each of the at least two conductive strips has substantially same length and width as remainder conductive strips of the at least two conductive strips; and
   a passivation layer encasing the substrate and the at least two conductive strips, wherein the at least two conductive strips are adapted to respond to an interrogation signal from a reader having a first polarization, with a response signal at a second polarization different than the first polarization,
   wherein resonant frequency of the sensor is inversely related to number of strips of the at least two conductive strips such that when the number of strips increases from 2 to 6, the resonant frequency is reduced from 2.9 GHz to 1.6 GHZ,
   wherein the at least two conductive strips are configured to simultaneously provide sensing and antenna functionalities; and
   wherein the passivation layer physically isolates the at least two conductive strips and the substrate from surrounding environment.

2. The sensor of claim 1, wherein each of the at least two conductive strips is made of metal.

3. The sensor of claim 2, wherein the metal is biodegradable including zinc.

4. The sensor of claim 1, wherein the substrate is made of acrylic.

5. The sensor of claim 1, wherein each of the at least two conductive strips is about 6 cm to about 10 cm long.

6. The sensor of claim 2, wherein the metal is non-biodegradable including copper.

7. The sensor of claim 1, wherein the lumped parameters are defined based on:

$$L_{meander} = 0.2L\left\{\left[1.4813 \log\left(\frac{2L}{a}\right)\right]^{1.012} - 0.6188\right\}\mu H$$

$$C_{meander} = \frac{C_{bend}}{N}$$

where N is the number of bends in the meandered profile,
L is the total length of the meander profile,
a is the radius of the trace, and
$C_{bend}$ is the capacitance between adjacent bends.

8. The sensor of claim 7, wherein the resistance of the sensor is determined based on:

$$R_{rad} = 34.15\left(2\pi\frac{(L-2wN)}{\lambda}\right)^{1.8}$$

where w is the gap between the bends, and
$\lambda$ is the wavelength.

9. The sensor of claim 8, wherein N is between 1 and 10.

10. The sensor of claim 1, wherein the passivation layer is a polymer coating.

11. A system of determining soil conditions, comprising:
one or more ground interrogating devices, each configured to radiate a wireless interrogating signal at a first polarization;
a plurality of ground-embedded battery-less and chipless sensors, each suitable for a subterranean application, comprising:
   a sensor body consisting of:
      a substrate,
      at least two conductive strips connected to each other and disposed in a meandered profile on the substrate, wherein each of the at least two conductive strips has substantially same length and width as remainder conductive strips of the at least two conductive strips, and
      a passivation layer encasing the substrate and the at least two conductive strips,
   wherein the at least two conductive strips are adapted to receive the interrogation signal from the one or more ground interrogating devices, and in response thereto provide a response signal at a second polarization different than the first polarization; wherein the response signal corresponds to a plurality of soil variable associated with soil conditions, and
   wherein resonant frequency of the sensor is inversely related to number of strips of the at least two conductive strips such that when the number of strips increases from 2 to 6, the resonant frequency is reduced from 2.9 GHz to 1.6 GHZ;

wherein the at least two conductive strips are configured to simultaneously provide sensing and antenna functionalities; and wherein the passivation layer physically isolates the at least two conductive strips and the substrate from surrounding environment;

a server configured to receive signals from the one or more ground interrogating devices; and at least one input/output device in communication with the server and configured to provide control signals to the one or more ground interrogating devices and to receive data associated with the soil variable associated with soil conditions.

12. The system of claim 11, wherein the at least two conductive strips are made of metal.

13. The system of claim 12, wherein the metal is biodegradable including zinc.

14. The system of claim 11, wherein the substrate is made of acrylic.

15. The system of claim 11, wherein the at least two conductive strips are about 6 cm to about 10 cm.

16. The system of claim 12, wherein the metal is non-biodegradable including copper.

17. The system of claim 11, wherein the lumped parameters are defined based on:

$$L_{meander} = 0.2L\left\{\left[1.4813 \log\left(\frac{2L}{a}\right)\right]^{1.012} - 0.6188\right\}\mu H$$

$$C_{meander} = \frac{C_{bend}}{N}$$

where N is the number of bends in the meandered profile,
L is the total length of the meander profile,
a is the radius of the trace, and
$C_{bend}$ is the capacitance between adjacent bends.

18. The system of claim 17, wherein the resistance of the sensor is determined based on:

$$R_{rad} = 34.15\left(2\pi\frac{(L-2wN)}{\lambda}\right)^{1.8}$$

where w is the gap between the bends, and
λ is the wavelength.

19. The system of claim 17, wherein N is between 1 and 10.

20. The system of claim 11, wherein the passivation layer is a polymer coating.

* * * * *